United States Patent [19]

Yano et al.

[11] Patent Number: 4,985,547

[45] Date of Patent: Jan. 15, 1991

[54] EXTERNAL SKIN CARE PREPARATION

[75] Inventors: Shinji Yano; Akira Kawamata, both of Utsunomiya; Yoshihiro Minematsu; Shuichi Akazaki, both of Funabashi; Mitsuko Zama, Tokyo; Genji Imokawa; Naotake Takaishi, both of Utsunomiya; Tsuyoshi Ohtomo, Funabashi; Takashi Komori, Tokyo, all of Japan

[73] Assignee: Kao Corporation, Tokyo, Japan

[21] Appl. No.: 163,835

[22] Filed: Mar. 3, 1988

[30] Foreign Application Priority Data

| Mar. 6, 1987 | [JP] | Japan | 62-51276 |
| Mar. 9, 1987 | [JP] | Japan | 62-53769 |
| Mar. 11, 1987 | [JP] | Japan | 62-56049 |
| Mar. 16, 1987 | [JP] | Japan | 62-60718 |
| Mar. 16, 1987 | [JP] | Japan | 62-60719 |
| May 28, 1987 | [JP] | Japan | 62-132054 |
| Jun. 2, 1987 | [JP] | Japan | 62-138727 |
| Jun. 30, 1987 | [JP] | Japan | 62-163682 |
| Jun. 30, 1987 | [JP] | Japan | 62-163683 |
| Jun. 30, 1987 | [JP] | Japan | 62-163685 |

[51] Int. Cl.$^5$ ............ C07C 103/10; C07C 103/00; A61K 7/00
[52] U.S. Cl. ............ 536/4.1; 536/17.2; 536/17.3; 536/17.5; 424/64; 424/70; 514/844; 514/846; 514/847; 514/969; 514/975
[58] Field of Search ............ 424/64, 70; 514/969, 514/975, 844, 846, 847; 536/4.1, 17.2, 17.3, 17.5

[56] References Cited

FOREIGN PATENT DOCUMENTS 48-72118 9/1973 Japan.
54-117421 9/1979 Japan.
54-144308 11/1979 Japan.
54-147937 11/1979 Japan.

Primary Examiner—Ronald W. Griffin
Attorney, Agent, or Firm—Oblon, Spivak, McClelland, Maier & Neustadt

[57] ABSTRACT

An external skin care preparation comprising a compound represented by the following general formula (I) or (II), or a salt thereof:

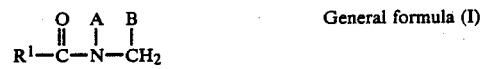

General formula (I)

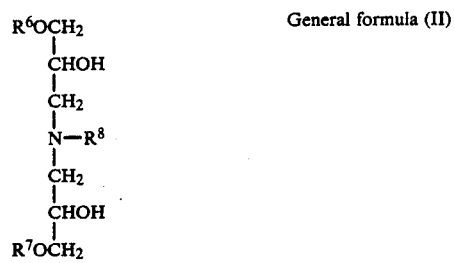

General formula (II)

wherein $R^1$ means an aliphatic hydrocarbon group having 9–25 carbon atoms, A and B denote specific groups respectively, $R^6$ and $R^7$ are individually an aliphatic hydrocarbon group having 10–26 carbon atoms, and $R^8$ denotes a group $-CH_2CH_2OH$, $-CH_2COOH$ or $-COCH_3$.

8 Claims, No Drawings

EXTERNAL SKIN CARE PREPARATION

BACKGROUND OF THE INVENTION (1) Field of the Invention

This invention relates to an external skin care preparation, and more specifically to an external skin care preparation which can enhance the water-retaining ability of the horny layer and improve skin roughness.

(2) Description of the Related Art

The water content of the horny layer has already been known to be critical for imparting moisture to the skin to maintain the skin smoothness and softness. The retention of water is said to rely upon a water-soluble component contained in the horny layer, namely, a free amino acid, organic acid, urea or inorganic ions. These materials have been incorporated either singly or in combination in medical external skin care preparations or cosmetic preparations with a view toward improving or avoiding skin roughness.

Besides, many humectants having high affinity with water have also been developed and have been used for similar purposes.

However, these humectants remain on the skin surface when they are applied to the skin, so that they serve to supply water to horny layer. Moreover, their effects are temporary and they are not such that can improve the water-retaining ability of the horny layer and can also avoid or cure skin roughness substantially.

SUMMARY OF THE INVENTION

Under the above circumstances, the present inventors have carried out an extensive investigation with a view toward solving the above problems. As a result, it has been found that a compound represented by the following general formula (I) or (II) or a salt thereof shows effects in improving the water-retaining ability of the horny layer significantly and the combined use of a surfactant with the compound or salt can enhance the effects further, leading to completion of this invention.

$$\underset{R^1-C-N-CH_2}{\overset{O\;\;A\;\;B}{\|\;\;|\;\;|}} \quad (I)$$

wherein $R^1$ means an aliphatic hydrocarbon group having 9–25 carbon atoms, A denotes a group $(CH_2)_l OH$ (l: integer of 3–6), a group $$\underset{X^2}{\overset{X^1\;\;X^3}{\underset{|}{-C}-CHOH}}$$

($X^1$, $X^2$, $X^3$: H, $C_{1-5}$-alkyl or hydroxyalkyl, individually), a group $(CH_2CH_2)_m H$ (m: integer of at least 2), a group $$\underset{}{\overset{R^2}{-CHCO_2Y}}$$

(Y: H or alkali metal; $R^2$: H, $-CH_3$,

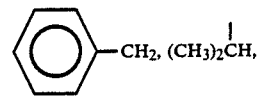

$(CH_3)_2CH$, $(CH_3)_2CHCH_2-$, $C_2H_5(CH_3)CHCH_2-$, $HOCH_2-$, $CH_3(HO)CH-$, $CH_3SCH_2CH_2-$, $YOCOCH_2-$, $YOCOCH_2CH_2-$,

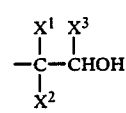

or a group $-CH_2CH_2OR^3$ [$R^3$: sugar residuum or group $$\underset{O^\ominus}{\overset{O}{\underset{\|}{-P}-OCH_2CH_2-\overset{Z^1}{\underset{Z^3}{N^\oplus-Z^2}}}}$$

($Z^1, Z^2, Z^3$: H, straight-chain or branched $C_{1-6}$-alkyl, or aralkyl)], and B stands for a group $$\underset{}{\overset{OR^4}{-CHCH_2OR^5}}$$

[$R^4$: H, sugar residuum, group $$\underset{O^\ominus}{\overset{O}{\underset{\|}{-P}-OCH_2CH_2-\overset{Z^1}{\underset{Z^3}{N^\oplus Z^2}}}}$$

($Z^1, Z^2, Z^3$: the defined above) or group $(CH_2CH_2O)_n H$ (n: integer of at least 1); $R^5$: $C_{8-28}$-aliphatic hydrocarbon group]or a group $$\underset{}{\overset{OH}{-CHR^5}}$$

($R^5$: as defined above), with a proviso that $X^1$, $X^2$, $X^3$ and $R^4$ do not mean H at the same time.

$$\begin{array}{c} R^6OCH_2 \\ | \\ CHOH \\ | \\ CH_2 \\ | \\ N-R^8 \\ | \\ CH_2 \\ | \\ CHOH \\ | \\ R^7OCH_2 \end{array} \quad (II)$$

wherein $R^6$ and $R^7$ mean individually an aliphatic hydrocarbon group having 10–26 carbon atoms and $R^8$ denotes a group —CH$_2$CH$_2$OH, —CH$_2$COOH or —COCH$_3$.

In one aspect of the invention, there is thus provided an external skin care preparation comprising a compound represented by the formula (I) or (II) or a salt thereof. The external skin care preparation may additionally contain a surfactant.

In another aspect of the invention, there is also provided a glycolipid derivative represented by the following general formula (Ie'):

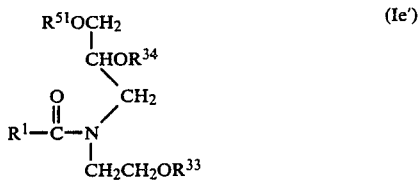

wherein R$^1$ means an aliphatic hydrocarbon group having 9–25, R$^{51}$ denotes an aliphatic hydrocarbon group having 10–26, and R$^{33}$ and R$^{34}$ are individually H or sugar residuum, with a proviso that R$^{33}$ and R$^{34}$ do not mean H at the same time.

Although details of the mechanism of action of the compound represented by the formula (I) or (II) or a salt thereof in the external skin care preparation of this invention has not been elucidated fully, it appears to reconstruct lipid membranes between horny cells to allow the horny layer to exhibit its water-retaining function.

Owing to the inclusion of the compound (I) or (II) or a salt thereof having such an action, the external skin care preparation according to the present invention can exhibit excellent effects for the improvement and prevention of skin roughness.

The above and other objects, features and advantages of the present invention will become apparent from the following description and the appended claims.

DETAILED DESCRIPTION OF THE INVENTION

Among compounds of the formula (I) useful in the practice of this invention, those represented by the following formula (Ia):

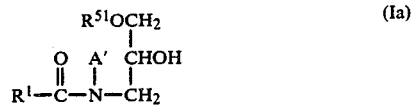

wherein R$^1$ has the same meaning as defined above, R$^{51}$ denotes an aliphatic hydrocarbon group having 10–26 carbon atoms, and A' is a group $(CH_2)_l$OH (l: as defined above) or

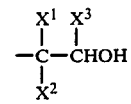

(X$^1$,X$^2$,X$^3$: as defined above), with a proviso that X$^1$,X$^2$ and X$^3$ do not mean H at the same time, can be prepared, for example, in accordance with the following reaction scheme.

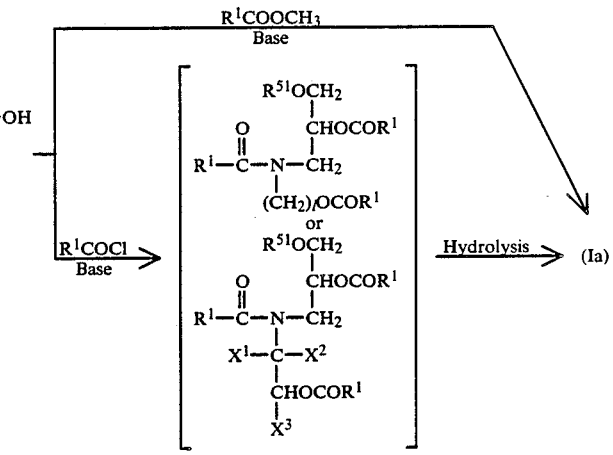

Namely, the compound (Ia) is prepared by obtaining the compound (IIIa) from its corresponding glycidyl ether and amino-alcohol in accordance with a process known per se in the art [Pol. J. Chem., 52, 1059(1978); ibid, 52, 1283(1978); Japanese Patent Laid-Open No. 117421/1979; ibid, 144308/1979; ibid, 147937/1979] and then selectively acylating the amino group of the compound (IIIa) or acylating the compound (IIIa) and then selectively hydrolyzing the ester moiety.

The reaction between the glycidyl ether and amino-alcohol may be carried out by stirring the glycidyl ether and the amino-alcohol at 25°–150° C. for several tens minutes to 5 hours either without any solvent or in a solvent of a lower alcohol such as methanol, ethanol, propanol or isopropanol. Illustrative examples of the amino-alcohol may include 3-amino-1-propanol, 4-amino-1-butanol, 5-amino-1-pentanol, 6-amino-1-hexanol, 3-amino-1,2-propanediol, tris(hydroxymethyl)aminomethane, 1-amino-2-propanol, 2-amino-1-propanol, 2-amino-1-butanol, 2-amino-1-pentanol, 2-amino-3-methyl-1-butanol, 2-amino-1-hexanol, 2-amino-2-methyl-1-propanol, 2-amino-2-methyl-1,3-propanediol and 2-amino-2-ethyl-1,3propanediol.

The selective acylation of the amino group of the compound (IIIa) may be achieved, for example, by reacting the methyl ester of a long-chain fatty acid with the compound (IIIa) in the presence of a base, such as alkali hydroxide or alkali carbonate, under normal pressure or a reduced pressure up to 0.01 Torr at 25°–150° C. for several tens minutes to 5 hours.

The non-selective acylation of the compound (IIIa) may be attained, for example, by reacting a long-chain fatty acid halide with the compound (IIIa) in the presence of pyridine, a tertiary amine or the like. The selective hydrolysis of the ester moiety of the resultant amide-ester derivative may be carried in a manner known per se in the art, using a base such as alkali hydroxide or alkali carbonate.

Of the compounds represented by the formula (I), those represented by the following formula (Ib):

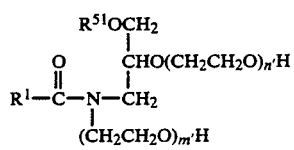

wherein $R^1$ has the same meaning as defined above, $R^{51}$ denotes an aliphatic hydrocarbon group having 10–26 carbon atoms, m' is an integer of at least 1, and n' stands for an integer of at least 0, with a proviso that m' and n' do not mean 1 and 0 respectively at the same time, may be prepared, for example, in accordance with the following reaction scheme.

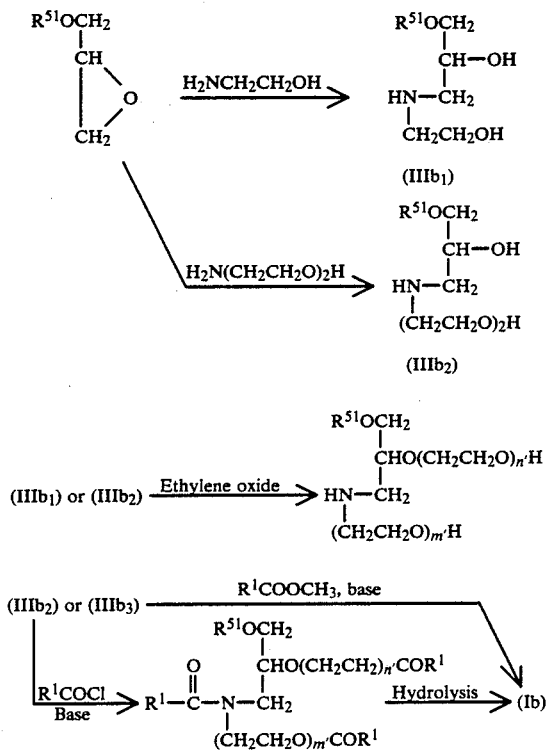

Likewise the preparation of the compound (IIIa), the compound (IIIb$_1$) or (IIIb$_2$) is obtained by reacting the corresponding glycidyl ether with the ethanolamine or 2-aminoethoxyethanol. By adding ethylene oxide further, the compound (IIIb$_3$) is obtained. The compound (Ib) is then prepared by selectively acylating the amino group of the compound (IIIb$_2$) or (IIIb$_3$) or by non-selectively acylating the compound (IIIb$_2$) or (IIIb$_3$) and then hydrolyzing the thus-acylated derivative in the same manner as in the preparation of the compound (Ia).

Among the compounds represented by the formula (I), those represented by the following formula (Ic):

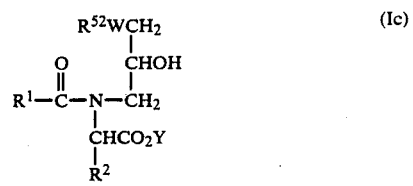

wherein $R^1$, $R^2$ and Y have the same meaning as defined above, $R^{52}$ denotes an aliphatic hydrocarbon group having 8–26 carbon atoms, and W is 0 or $CH_2$, may be prepared, for example, by a known process such as that disclosed in Japanese Patent Laid-Open No. 72118/1973 in accordance with the following reaction scheme.

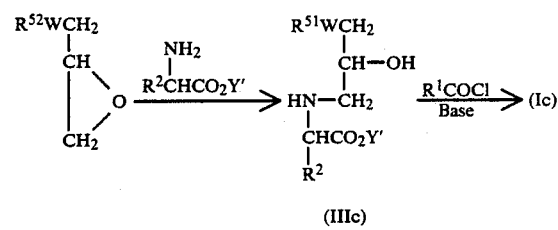

wherein Y' means an alkali metal or ester residuum.

Namely, the amido derivative (Ic) is prepared by reacting an alkali metal salt or ester of an amino acid with the glycidyl ether or α-olefin epoxide derivative to form the compound (IIIc) and then acylating the compound (IIIc).

As the amino acid, may be mentioned glycine, alanine, phenylalanine, valine, leucine, isoleucine, serine, methionine, aspartic acid, glutamic acid, histidine, tryptophan or the like. Its alkali metal salt may be the lithium, sodium or potassium salt. Illustrative examples of its ester may include lower alkyl esters such as the methyl, ethyl, n-propyl, iso-propyl and butyl esters, the phenyl ester and the benzyl ester. Among the compounds represented by the formula (I), those represented by the following formula (Id):

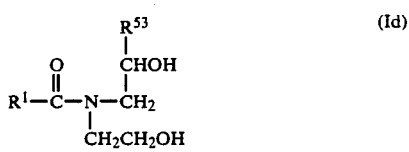

wherein $R^1$ has the same meaning as defined above, and $R^{53}$ denotes an aliphatic hydrocarbon group having 8–24 carbon atoms, may be prepared, for example, in accordance with the following reaction scheme.

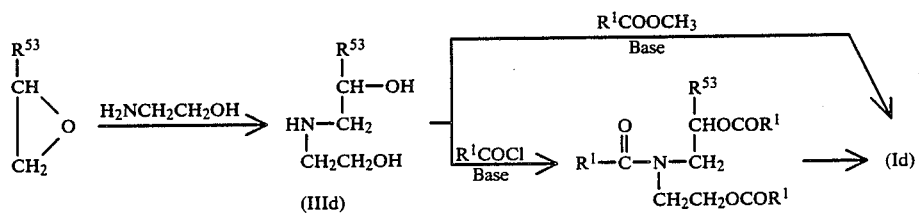

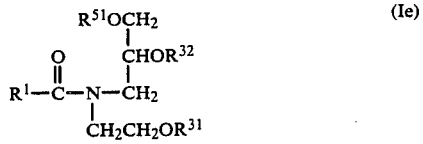
(IIId)

Namely, the compound (Id) is prepared by selectively acylating the amino group of the compound (IIId), which has been obtained by a reaction between an α-olefin epoxy compound and ethanolamine, or nonselectively acylating the compound (IIId) and then hydrolyzing the thus-acylated derivative in the same manner as in the preparation of the compound (Ia). Further, among the compounds (I), those represented by the following general formula (Ie):

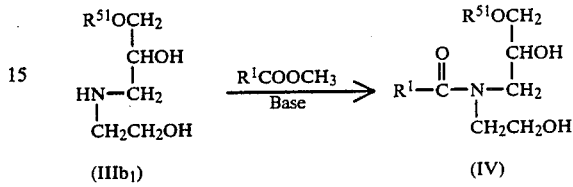

wherein $R^1$ have the same meaning as defined above, $R^{51}$ means an aliphatic hydrocarbon group having 10–26 carbon atoms, and $R^{31}$ and $R^{32}$ denote individually H, sugar residuum or group

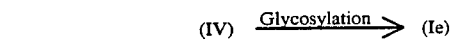

($Z^1$, $Z^2$, $Z^3$: as defined above), with a proviso that $R^{31}$ and $R^{32}$ are not H at the same time and one of $R^{31}$ and $R^{32}$ is other than the sugar residuum when the other is the group

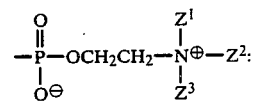

(1) Where $R^{31}$ or $R^{32}$ is a sugar residuum:

(IV) $\xrightarrow{\text{Glycosylation}}$ (Ie)

(2) Where $R^{31}$ or $R^{32}$ is a group

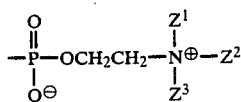

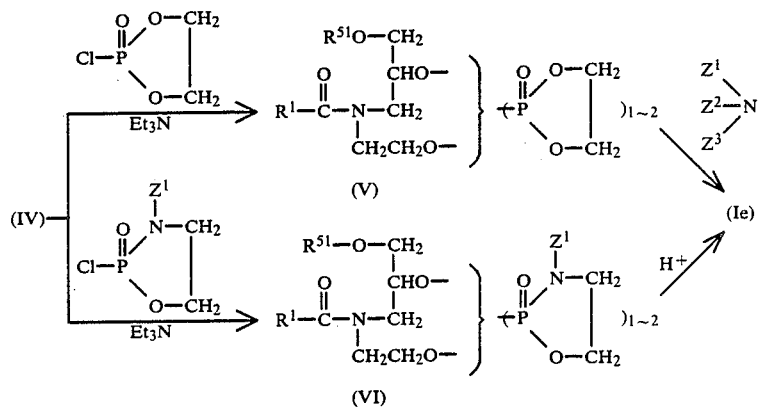

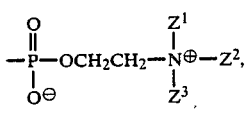

may be prepared, for example, in accordance with the following reaction scheme.

Namely, the compound (Ie) in which $R^{31}$ or $R^{32}$ is a sugar residuum is obtained by selectively acylating the amino group of the compound (IIIb$_1$) into the compound (IV) and then glycosylating the compound (IV).

The glycosylation of the compound (IV) may be effected by a method known per se in the art, for example, by the Koenigs-Knorr synthesis, triflate process, trichloroacetimidate process, fluorinated glycoside process, or the like. The above glycosylation reaction, the glycosylation reaction is effected after protecting either one of the primary and secondary hydroxyl groups with suitable protecting groups. Deprotection of the protecting groups subsequent to the reaction affords a compound of the formula (Ie) in which one of $R^{31}$ and $R^{32}$ is a sugar residuum and the other is a hydrogen atom. It is preferable to protect with suitable protecting groups the hydroxyl groups of a sugar derivative to be reacted with the compound (IV).

As exemplary sugars corresponding to the sugar residua represented by $R^{31}$ and $R^{32}$ respectively in the formula (Ie), may be mentioned hexoses such as glucose, galactose, mannose, fructose, sorbose, allose, 2-deoxyglucose, 2-deoxygalactose and fucose; pentoses such as arabinose, lyxose, ribose, deoxyribose, ribulose, xylose and xylulose; disaccharides such as sucrose, cellobiose, lactose, maltose, melibiose, parathiose, trehalose and turanose; trisaccharides such as maltotriose; amino sugars such as glucosamine, galactosamine and mannosamine; N-acylated amino sugars such as N-acetylglucosamine, N-acetylgalactosamine and N-acetylmannosamine; glucocarboxylic acids such as glucuronic acid, galacturonic acid, N-acetylmuramic acid and N-acetylneuraminic acid; etc.

The following are typical examples of glycosylation in the present invention.

(1) Reaction making use of DL-glucose:

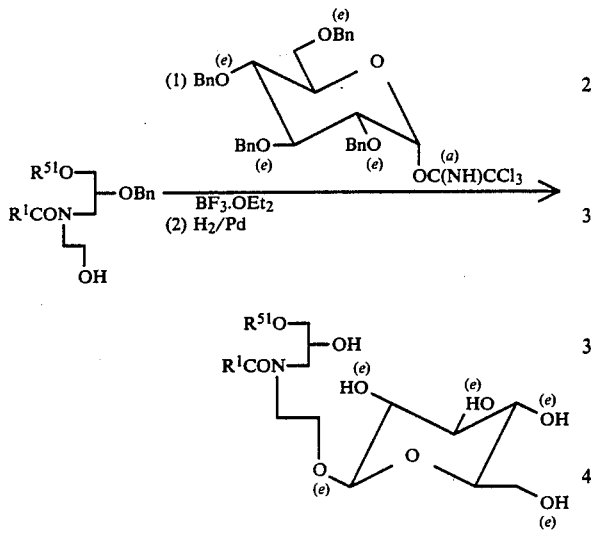

(2) Reaction making use of DL-fucose:

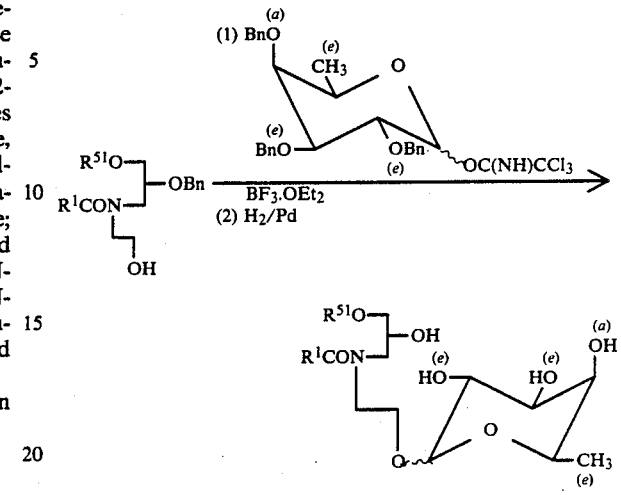

(3) Reaction making use of DL-ribose:

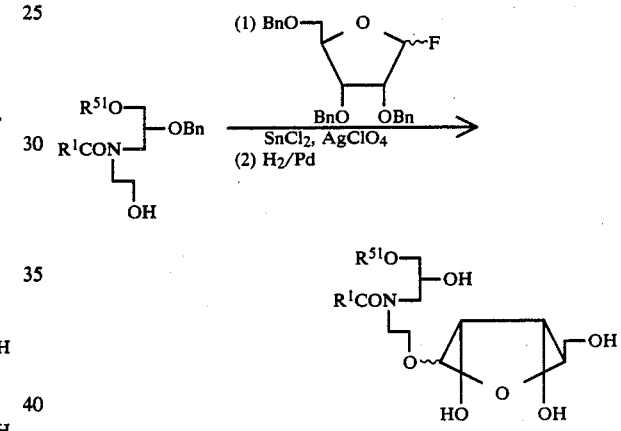

(4) Reaction making use of lactose:

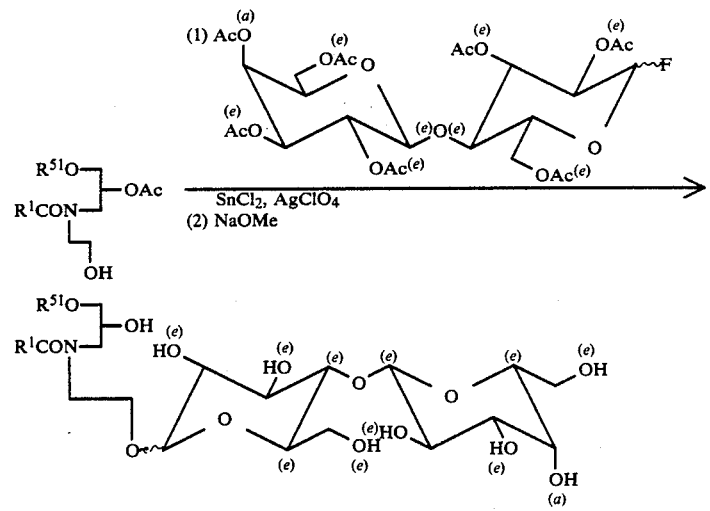

(5) Reaction making use of maltotriose:

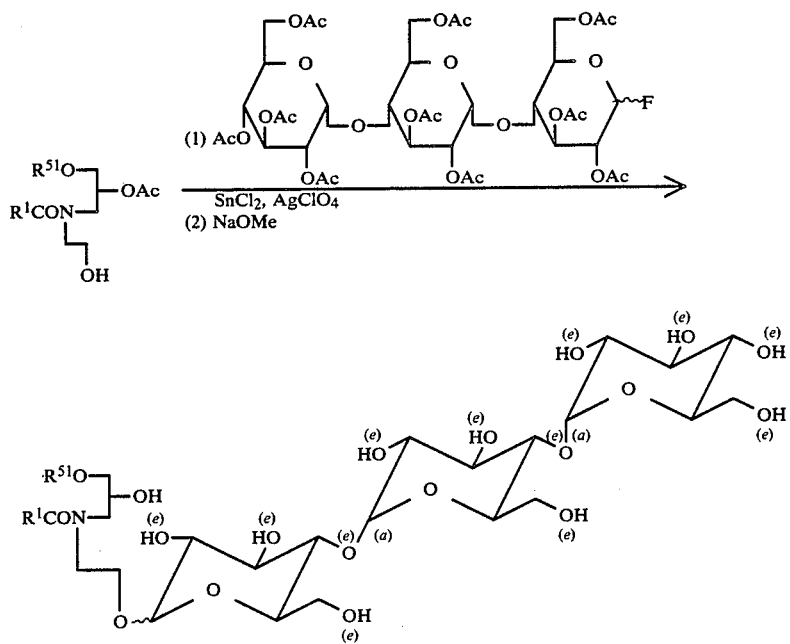

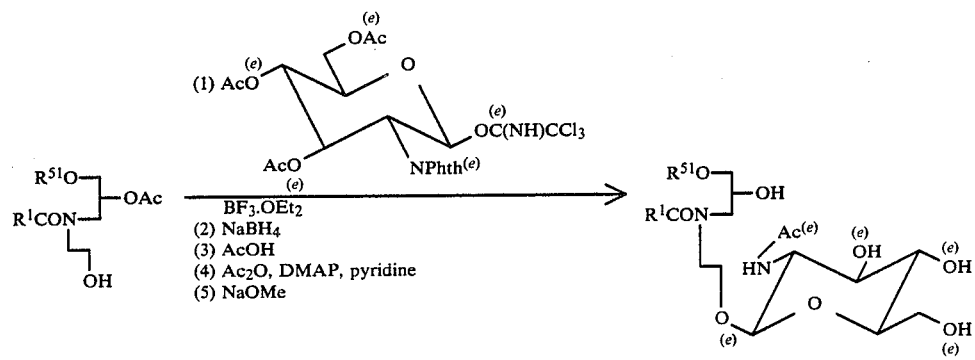

(6) Reaction making use of glucosamine:

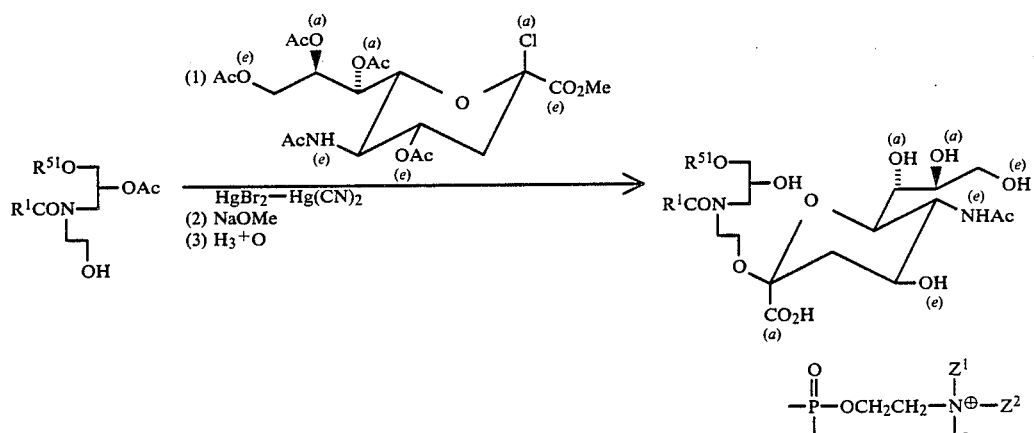

(7) Reaction making use of N-acetylneuraminic acid:

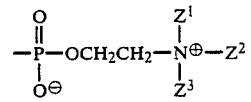

In the above formulae, the abbreviations have the following meaning: Et: ethyl, Me: methyl, Bn: benzyl, Ac: acetyl, Phth: phthaloyl, DMAP: N,N-dimethylaminopyridine.

Further, the compound (Ie) in which $R^{31}$ or $R^{32}$ may be prepared via the dioxaphosphoran derivative (V) or oxaazaphosphoran derivative (VI) in accordance with a known process [N. T. Thuong, P. Chabrier, Bull.

Soc. Chim. Fr., 1974, 667; N.S. Chandrakumar, J. Hajdu, Tetrahedron Lett., 22, 2949 (1981)].

The compounds of the formula (II) useful in the practice of this invention have already been known. Those represented by the formula (II) in which $R^8$ is a group $-CH_2CH_2OH$ or $-COCH_3$ can be prepared, for example, by the process described in Polish. J. Chem., 52, 1059(1978) referred to above. On the other hand, the compound of the formula (II) in which $R^8$ is a group $-CH_2COOH$ can be prepared, for example, in accordance with the process of East German Patent No. 92940 (1973).

As illustrative examples of the salt of the compound (I) or (II) useful in the practice of this invention, may be mentioned those usable in cosmetic compositions, such as alkali metal salts.

No particular limitation is imposed on the proportion of the compound represented by the formula (I) or (II) or a salt thereof in the external skin care preparation. In the case of an emulsion-type external skin care preparation, its proportion may preferably be 0.001–50 wt.% (hereinafter indicated merely by "%"), notably, 0.1–20% of the whole preparation. In the case of an oil-base external skin care preparation containing a liquid hydrocarbon such as squalene as a base, its proportion may preferably be 1–50%, notably, 5–25%.

As a surfactant suitable for incorporation in the external skin care preparation, any one of non-ionic surfactants, anionic surfactants and amphoteric surfactants may be mentioned. Of these, non-ionic surfactants are especially suitable.

As exemplary non-ionic surfactants, may be mentioned polyoxyethylene alkyl ethers, polyoxyethylene alkylphenyl ethers, polyoxyethylene fatty acid esters, sorbitan fatty acid esters, polyoxyethylene sorbitan fatty acid esters, fatty acid monoglycerides, glyceryl ethers, etc. Among these, glyceryl ethers represented by the following general formula (VII):

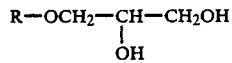
(VII)

wherein R means an alkyl group having 8–24 carbon atoms are preferred. Particularly preferred are glyceryl ethers of the formula (VII) in which R is represented by the following formula (VIII):

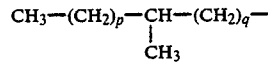
(VIII)

wherein p means an integer of 4–10, q denotes an integer of 5–11, and p+q is 11–17 and is distributed with a peak at p=7 and q=8.

The proportion of the surfactant may be 0.01–20% of the whole preparation, with 0.1–5% being particularly preferred.

External skin care preparations according to this invention may be classified roughly into medicinal external skin care preparation and cosmetic preparations in accordance with their manner of use.

As exemplary medicinal external skin care preparations, may be mentioned various ointments containing one or more medicinally-effective ingredients. Ointments include both those containing an oily base as a base and those containing an oil/water or water/oil emulsion-type base as a base. No particular limitation is imposed on oily bases. Plant oils, animal oils, synthetic oils, fatty acids, natural and synthetic glycerides, etc. may be mentioned by way of example. No specific limitation is imposed on medicinally-effective ingredients. For example, one or more of analgesic and antiphlogistic agents, antipruritics, disinfectants, astringents, emollients, hormones and the like may be used suitably as needed.

Where used as a cosmetic preparation, it is possible to mix in addition to the essential ingredients those employed routinely as cosmetic ingredients such as oily substance, moisturizer, ultraviolet absorbent, alcohol, chelating agent, pH regulator, antiseptic, thickener, pigment, perfume base and the like in combination as needed.

As cosmetics, skin cosmetic preparations of various forms may be formulated including, for example, water-/oil or oil/water type emulsified cosmetics, creams, cosmetic emulsions, toilet waters, oily cosmetics, lip sticks, foundations, skin cleansing preparations, hair tonics, hair styling preparations, hair grooming preparations, hair growth stimulants, etc.

Having generally described the invention, a more complete understanding can be obtained by reference to certain specific examples, which are provided herein for purposes of illustration only and are not intended to be limiting unless otherwise specified.

EXAMPLES

The present invention will hereinafter be described by the following Referential Examples and Examples.

Referential Example 1:

Synthesis of N-(3-hexadecyloxy-2-hydroxypropyl)-N-3-hydroxypropylhexadecanamide (Ia$_1$) [in the formula (Ia), $R^1$: $C_{15}H_{31}$, $A'$:$\text{-(CH}_2)_3$OH, $R^{51}$: $C_{16}H_{33}$]:

In a 200 ml four-necked flask equipped with a mechanical stirrer, dropping funnel, thermometer, reflux condenser and nitrogen inlet tube 25.0 g (0.333 mol) of 3-amino-1-propanol and 50 g of ethanol were placed. While stirring and heating the mixture at 80° C. in a nitrogen atmosphere, a solution of 10.0 g (0.034 mol) of hexadecyl glycidyl ether in 30 g of ethanol was added dropwise over 2 hours. After the addition was completed, the heating and stirring were continued for additional 30 minutes under the same conditions. A distillation apparatus was connected to the flask so as to distill off the ethanol and unreacted 3-amino-1-propanol under reduced pressure, thereby obtaining 12.5 g of a pale yellow solid. A 7.47 g (equivalent to 0.020 mol) portion of the crude product was separated, to which 0.056 g of potassium hydroxide was added. While stirring the resultant mixture at 80° C./20 Torr, 5.42 g (0.020 mol) of methyl hexadecanoate was added dropwise over 1 hour. After the addition was completed, the mixture was stirred under heat for 1 hour under the same conditions to obtain 12.2 g of a pale yellow crude product. The crude product was recrystallized once from 120 g of hexane and then once from 100 g of methanol, thereby obtaining 9.18 g of the intended compound (Ia$_1$) as colorless powder (overall yield: 75%). Melting point: 82.4°–83.4° C.

IR (KBr, cm$^{-1}$): 3250, 2920, 2854, 1605, 1470, 1119.

$^1$H-NMR (CDCl$_3$, δ): 0.87(6H,t), 1.1–2.0(56H,m), 2.42(2H,t), 3.2–4.4(13H,m).

Elemental analysis: Calculated: C, 74.57%; H, 12.68%; N, 2.29%. Found: C, 74.67%; H, 12.73%; N, 2.21%.

Referential Example 2:

Synthesis of N-(3-hexadecyloxy-2-hydroxypropyl)-N-6-hydroxyhexylhexadecanamide (Ia2) [in the formula (Ia), $R^1$: $C_{15}H_{31}$, A': $-(CH_2)_6OH$, $R^{51}$ $C_{16}H_{33}$]:

In a 200 ml four-necked flask equipped with a mechanical stirrer, dropping funnel, thermometer, reflux condenser and nitrogen inlet tube 58.0 g (0.50 mol) of 6-amino-1-hexanol and 150 g of ethanol were placed. While stirring and heating the mixture at 80° C. in a nitrogen atmosphere, a solution of 15.0 g (0.050 mol) of hexadecyl glycidyl ether in 50 g of ethanol was added dropwise over 1 hour. After the addition was completed, the heating and stirring were continued for additional 30 minutes under the same conditions. A distillation apparatus was connected to the flask so as to distill off the ethanol and unreacted 6-amino-1-hexanol under reduced pressure, thereby obtaining 15.8 g of a pale yellow solid. A 8.3 g (equivalent to 0.020 mol) portion of the crude product was separated, and was then dissolved in 200 ml of methylene chloride, followed by an addition of 4.8 g (0.06 mol) of pyridine. Under water cooling, 16.5 g (0.06 mol) of hexadecanoyl chloride was added dropwise over about 30 minutes. After the addition was completed, the mixture was stirred at room temperature for 1 hour. The reaction mixture was washed with water to remove pyridinium chloride, and the solvent was then distilled off to obtain 22.6 g of an amide-ester derivative.

Thereafter, the amide-ester derivative was dissolved in 400 g of 95% aqueous ethanol and 2.24 g (0.04 mol) of potassium hydroxide. The resultant mixture was stirred at 50° C for 1 hour. Chloroform-soluble portions were extracted from the reaction mixture and then purified by flash chromatography on a silica gel column, thereby obtaining 9.0 g (0.0138 mol) of the title compound as colorless powder (overall yield: 52.4%).

Melting point: 78.8°–79.8° C.

IR (KBr, cm$^{-1}$): 3334, 2920, 2854, 1623, 1467, 1113.

$^1$H-NMR (CDCl$_3$, $\delta$): 0.87(6H,t), 1.2–1.9(62H,m), 2.41(2H,t), 3.1–4.3(13H,m).

Elemental analysis: Calculated: C, 75.28%; H, 12.79%; N, 2.14%. Found: C, 75.33%; H, 12.83%; N, 2.09%.

Referential Example 3:

Synthesis of N-(3-hexadecyloxy-2-hydroxypropyl)-N-2,3-dihydroxypropylhexadecanamide (Ia3) [in the formula (Ia), $R^1$: $C_{15}H_{31}$, A': $-CH_2CH(OH)CH_2OH$, $R^{51}$: $C_{16}H_{33}$]:

In a 200 ml four-necked flask equipped with a mechanical stirrer, dropping funnel, thermometer and reflux condenser were 48.3 g (0.50 mol) of 3-amino-1,2-propanediol and 150 g of ethanol. While stirring and heating the mixture at 80° C., a solution of 15.0 g (0.050 mol) of hexadecyl glycidyl ether in 150 g of ethanol was added dropwise over 1 hour. After the addition was completed, the heating and stirring were continued for additional 1 hour under the same conditions. The ethanol and unreacted 3-amino-1,2-propanediol were distilled off under reduced pressure, thereby obtaining 19.8 g of pale yellow solid.

Thereafter, the crude product was dissolved in 300 g of methylene chloride, followed by an addition of 15.8 g (0.20 mol) of pyridine. Under water-cooling, 54.8 g (0.20 mol) of hexadecanoyl chloride was added over about 30 minutes. After the addition was completed, the contents were stirred at room temperature for 1 hour. The reaction mixture was then washed with water to remove pyridinium chloride, and the solvent was distilled off to obtain 64.0 g of an amide-ester derivative. The amide-ester derivative was thereafter dissolved in 500 g of 95% aqueous ethanol, to which was added 8.4 g (0.15 mol) of potassium hydroxide. The mixture was stirred at 50° C. for 1 hour. Chloroform-soluble portions were extracted from the reaction mixture and then purified by flash chromatography on a silica gel column, thereby obtaining 17.3 g (0.028 mol) of the title compound (Ia3) as colorless powder.

Yield: 56%.

Melting point: 81.9°–83.3° C.

IR (KBr, cm$^{-1}$): 3370, 3292, 2920, 2854, 1608, 1470, 1113.

$^1$H-NMR (CDCl$_3$, $\delta$): 0.87(6H,t), 1.1–1.8(54H,m), 2.42(2H,t), 3.2–4.4(15H,m).

Elemental analysis: Calculated: C, 72.67%; H, 12.36%; N, 2.23%. Found: C, 73.02%; H, 12.41%; N, 2.18%.

Referential Example 4:

Synthesis of N-(3-hexadecyloxy-2-hydroxypropyl)-N-2-hydroxyethoxyethylhexadecanamide (Ib1) [in the formula (Ib), m': 2, n': 0, $R^1$: $C_{15}H_{31}$, $R^{51}$ $C_{16}H_{33}$]:

In a 200 ml four-necked flask equipped with a mechanical stirrer, dropping funnel, thermometer and reflux condenser were 27.4 g (0.26 mol) of 2-aminoethoxy-ethanol and 100 g of ethanol were placed. While stirring and heating the mixture at 80° C., a solution of 15.0 g (0.050 mol) of hexadecyl glycidyl ether in 50 g of ethanol was added dropwise over 2 hours. After the addition was completed, the heating and stirring were continued for additional 1 hour under the same conditions. The ethanol and unreacted 2-aminoethoxyethanol were distilled off under reduced pressure, thereby obtaining 17.7 g of an intermediate, N-(3-hexadecyloxy-2-hydroxypropyl)-N-2-hydroxyethylamine as pale yellow solid.

Thereafter, the intermediate was dissolved in 300 g of methylene chloride, followed by an addition of 11.9 g (0.15 mol) of pyridine. Under water-cooling, 41.1 g (0.15 mol) of hexadecanoyl chloride was added over about 30 minutes. After the addition was completed, the mixture was stirred at room temperature for 1 hour. The reaction mixture was then washed with water to remove pyridinium chloride, and the solvent was distilled off to obtain 53.8 g of an amide-ester derivative. The amide-ester derivative was thereafter dissolved in 400 g of 95% aqueous ethanol, to which 5.6 (0.10 mol) of potassium hydroxide was added. The mixture was stirred under heat at 40° C. for 30 minutes.

A chloroform-soluble fraction was extracted from the reaction mixture and then purified by flash chromatography on a silica gel column, thereby obtaining 17.3 g (0.027 mol) of the title compound (Ib1) as colorless crystals.

Overall yield: 56% (based on the hexadecyl glycidyl ether).

Melting point: 68.0–69.3° C.

IR (KBr, cm$^{-1}$): 3406, 2920, 2854, 1647, 1473, 1119.

$^1$H-NMR (CDCl$_3$, $\delta$): 0.87(6H,t), 1.1–1.8(54H,m), 2.40(2H,t), 3.3–4.4(17H,m).

Elemental analysis: Calculated: C, 72.96%; H, 12.40%; N, 2.18%. Found: C, 73.17%; H, 12.44%; N, 2.16%.

Referential Example 5:

Synthesis of N-(2-hydroxyethyl)-N-2-hydroxyhexadecyloctadecanamide (Id₁) [in the formula (Id), $R^1$: $C_{17}H_{35}$, $R^{53}$: $C_{14}H_{29}$]:

In a 500 ml four-necked flask equipped with a mechanical stirrer, dropping funnel, thermometer, reflux condenser and nitrogen inlet tube, 117 g (1.91 mol) of monoethanolamine and 117 g of ethanol were placed. While stirring and heating the mixture at 80° C. in a nitrogen atmosphere, a solution of 26.8 g (0.10 mol) of 1,2-epoxyoctadecane in 53.6 g of ethanol was added dropwise over 90 minutes. After the addition was completed, the heating and stirring were continued for additional 1 hour under the same conditions. A distillation apparatus was connected to the flask so as to distill off the ethanol and unreacted ethanolamine under reduced pressure. The residue was recrystallized from 250 ml of methanol, thereby obtaining 24.0 g of a long-chain ethanolamine intermediate as a pale yellow solid.

A 20.0 g (0.060 mol) portion of the crude product was separated, to which 0.225 g of potassium hydroxide was added. While stirring the resultant mixture at 80° C./20 Torr, 18.0 g (0.060 mol) of methyl octadecanoate was added dropwise over 1 hour. After the addition was completed, the mixture was stirred under heat for 1 hour under the same conditions to obtain a crude product as pale yellow solid. It was then purified by flash chromatography on a silica gel column, thereby obtaining 18.5 g (0.031 mol) of the title compound (Id₁) as colorless crystals.

Overall yield: 62.0% (based on the 1,2-epoxyoctadecane).

Melting point: 72.3°–73.8° C.

IR (KBr, cm⁻¹): 3436, 2920, 2854, 1602, 1473, 1080.

¹H-NMR (CDCl₃, δ): 0.87(6H,t), 1.1–1.7(60H,m), 2.37(2H,t), 3.1–4.1(9H,m).

Elemental analysis: Calculated: C, 76.58%; H, 13.02%; N, 2.35%. Found: C, 76.78%; H, 13.05%; N, 2.28%.

Referential Example 6:

Synthesis of N-(3-hexadecyloxy-2-hydroxypropyl)-N-(2-O-glucopyranosyl)ethylhexadecanamide (Ie₁) [in the formula (Ie), $R^1$ $C_{15}H_{31}$, $R^{31}$: glucopyranosyl, $R^{32}$: H, $R^{51}$: $C_{16}H_{33}$]:

(a) Synthesis of N-(3-hexadecyloxy-2-hydroxypropyl)-N-2-hydroxyethylhexadecanamide (IVa) [in the formula (IV), $R^1$ $C_{15}H_{31}$, $R^{51}$: $C_{16}H_{33}$]:

In a 5 l four-necked flask equipped with a mechanical stirrer, dropping funnel, thermometer, reflux condenser and nitrogen inlet tube, 1637 g (26.8 mol) of ethanolamine and 327 g (7.11 mol) of ethanol were placed. While stirring and heating the mixture at 80° C. in a nitrogen atmosphere, 400 g (1.34 mol) of hexadecyl glycidyl ether was added dropwise over 3 hours. After the addition was completed, the heating and stirring were continued for additional 30 minutes under the same conditions. A distillation apparatus was connected to the flask so as to distill off the ethanol and unreacted ethanolamine under reduced pressure (79°–81° C./20 Torr). A crude product was added with 3.76 g (0.067 mol) of potassium hydroxide. While stirring the resultant mixture at 80° C./20 Torr, 362.3 g (1.34 mol) of methyl hexadecanoate was added dropwise over 3 hours. After the addition was completed, the mixture was stirred under heat for 1 hour under the same conditions to obtain 801 g of a crude product as a pale yellow solid. The crude product was recrystallized once from hexane and then twice from ethanol, thereby obtaining 649 g of the title compound (IVa) as colorless powder (yield: 81%).

Melting point: 74°–76° C.

IR (KBr, cm¹): 3320(br.), 2924, 2852, 1616, 1468, 1112, 1062.

¹H-NMR (CDCl₃, δ): 0.86(6H,t), 1.0–1.6(54H,m), 2.2–2.5(2H,m), 3.2–4.1(13H,m).

Elemental analysis: Calculated: C, 74.31%; H, 12.64%; N, 2.34%. Found: C, 74.12%; H, 12.70%; N, 2.23%.

(b) Synthesis of N-(3-hexadecyloxy-2-hydroxypropyl)-N-2-triphenylmethoxyethylhexadecanamide:

In a 500 ml four-necked flask equipped with a mechanical stirrer, dropping funnel, thermometer, reflux condenser and nitrogen inlet tube, 59.81 g (0.1 mol) of N-(3-hexadecyloxy-2-hydroxypropyl)-N-2-hydroxyethylhexadecanamide (IVa) obtained in the step (a), 28.73 g (0.101 mol) of triphenylmethyl chloride and 300 ml of dry dichloromethane were stirred under nitrogen. A solution of 8.70 g (0.11 mol) of pyridine in 50 ml of dry dichloromethane was added dropwise to the above-prepared mixture over about 5 minutes, followed by heating under reflux at 40° C. for 6 hours. After the reaction was completed, the reaction mixture was cooled down, and precipitated pyridinium chloride was filtered off. The filtrate was washed four times with 100 ml of water and then dried over anhydrous sodium sulfate. The solvent was distilled off to obtain 77.11 g of a crude product as a colorless wax. The crude product was purified by flash chromatography on a silica gel column (silica gel: 230–400 mesh, 1 kg; solvent: dichloromethane/ethyl acetate=19/1), thereby obtaining 59.37 g of the title compound as colorless wax (yield: 70.7%).

Melting point: 46°–47° C.

IR (KBr, cm⁻¹): 3412, 3058, 3028, 2926, 2854, 1653, 1626, 1473, 1452, 1083, 705.

¹H-NMR (CDCl₃, δ): 1.86(6H,t), 1.0–1.6(54H,m), 2.2–2.5(2H,m), 3.2–4.1(12H,m), 7.2–7.5(15H,m).

(c) Synthesis of N-(2-benzyloxy-3-hexadecyloxypropyl)-N-2-hydroxyethylhexadecanamide:

In a 200 ml four-necked flask equipped with a stirrer, dropping funnel, thermometer, reflux condenser and nitrogen inlet tube, 58.82 g (0.07 mol) of N-(3-hexadecyloxy-2-hydroxypropyl)-N-2-triphenylmethoxyethyl hexadecanamide obtained in the step (b) was dissolved by 100 ml of N,N-dimethylformamide under nitrogen. The resultant solution was then added with 5.6 g (0.14 mol) of sodium hydride (as 60% solution in a mineral oil), followed by stirring at room temperature for 3 hours. After foaming had ceased, the mixture was heated to 60° C. and 17.90 g (0.14 mol) of benzyl chloride was added over 20 minutes. After completion of the dropwise addition, the mixture was stirred at 60° C. for 1.5 hours. After completion of the reaction, water was added dropwise under nitrogen to decompose excess sodium hydride. The reaction mixture was then poured into 500 ml of water. The resultant mixture was extracted with hexane. The hexane layer was washed twice with water and once with saturated aqueous sodium chloride, and was dried over anhydrous sodium sulfate. The solvent was distilled off to obtain 72.8 g of a crude product as a pale yellow oil. The crude product was purified by flash chromatography on a silica gel column (silica gel: 230–400 mesh, 1 kg; solvent: hexane/ethyl acetate=9/1), thereby obtaining 59.5 g of N-(2-benzyloxy-3-hexadecyloxypropyl)-N-2-triphenylmethoxyethylhexadecanamide as a pale yellow oily wax.

Under nitrogen, 55.83 g (0.06 mol) of the above compound, 6 ml (0.072 mol) of concentrated hydrochloric acid and 100 ml of dioxane were stirred at room temperature for 9 hours. After completion of the reaction, the dioxane was distilled off, 100 ml of dichloromethane was added, and the mixture was then neutralized with aqueous sodium bicarbonate. Subsequent to the collection of a dichloromethane layer, the dichloromethane solution was washed with saturated aqueous sodium chloride and then dried over anhydrous sodium sulfate. The solvent was thereafter distilled off to obtain 58.02 g of a crude product as a pale yellow oil. The crude product was purified by flash chromatography on a silica gel column and further by medium-pressure liquid chromatography, thereby obtaining 14.17 g of the title compound as a colorless wax (yield: 31.4%).

Melting point: 39°-40° C.
IR (KBr,cm$^{-1}$): 3412, 2920, 2854, 1647, 1626, 1473, 1116, 1089, 1032.
$^1$H-NMR (CDCl$_3$δ): 0.86(6H,t), 1.1–1.5(54H,br.s), 2.26(2H,m), 3.3–3.8(12H,m), 4.51(1H, d,J=12.0Hz), 4.64(1H,dd,J=12.0, 1.6Hz), 7.31(5H,br.s).

(d) Synthesis of N-(3-hexadecyloxy-2-hydroxypropyl)-N-(2-O-glucopyranosyl)ethylhexadecanamide (Ie$_1$) [In the formula (Ie), R$^1$: C$_{15}$H$_{31}$, R$^{31}$: glucopyranosyl, R$^{32}$: H, R$^{51}$: C$_{16}$H$_{33}$]:

In a 100-ml round bottom flask equipped with a mechanical stirrer, calcium chloride tube and dropping funnel, 1.08 g (1.57 mmol) of N-(2-benzyloxy-3-hexadecyloxypropyl)-N-2-hydroxyethylhexadecanamide obtained in the above step c) and 1.40 g (2.04 mmol) of O-(2 3,4,6-tetra-0-benzyl-α-D-glucopyranosyl) trichloroacetoimidate prepared by a known process [Liebig's Annalen der Chemie, 1249(1983)]were dissolved in 10 ml of dry dichloromethane. The reaction mixture was then stirred at room temperature. A solution of 0.29 g (2.04 mmol) of boron trifluoride diethyl etherate in 1 ml of dry dichloromethane was added to the mixture over 5 minutes. The resultant mixture was stirred at room temperature for 1 hour. After completion of the reaction, the reaction mixture was neutralized with a saturated aqueous sodium bicarbonate and then added with 40 ml of dichloromethane. The dichloromethane layer was washed with saturated aqueous sodium chloride and then dried over anhydrous sodium sulfate. The solvent was thereafter distilled off to obtain 2.215 g of a crude product as a pale yellow oil. The crude product was purified by medium-pressure liquid chromatography to obtain 1.514 g of a pentabenzylglycoside derivative as a colorless oil. In a mixed solvent of 100 ml of ethanol and 50 ml of methanol 1.21 g (1.0 mmol) of the thus-obtained pentabenzylglycoside derivative and 1.0 g of palladium black were suspended. In an 200 ml autoclave, the pentabenzylglycoside derivative was subjected to hydrogenation at 24°-28° C. for 7 hours under a hydrogen pressure of 112-127 Kg/cm$^2$. Chloroform was added to the reaction mixture to dissolve a white solid suspended therein. After separation of the palladium black by filtration, the solvent was distilled off to obtain 0.6 g of an amorphous crude product as a pale yellow solid. The crude product was purified by medium-pressure liquid chromatography (silica gel: 25-40 μm, 75 g; developer: chloroform/methanol=50/1), thereby obtaining 0.537 g of the title compound (Ie$_1$) as a colorless amorphous solid (yield: 56.5%). The thus-obtained compound was a mixture of the α-glucopyranosyl and δ-glucopyranosyl derivative at a ratio of about 1:9.

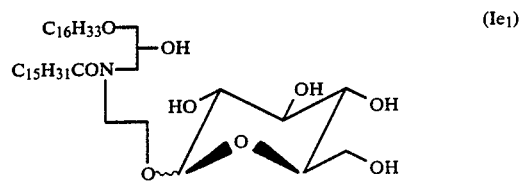
(Ie$_1$)

Melting point: 153°-154° C.
IR (KBr,cm$^{-1}$): 3416, 2920, 2852, 1626, 1470, 1106, 1080, 1038.
$^1$H-NMR (CDCl$_3$, δ): 0.86(6H,t), 1.1–1.7(60H,br.s), 2.2–6.0(25H,br.s).
Elemental analysis: Calculated: C, 67.94%; H, 11.27%; N, 1.84%. Found: C, 67.68%; H, 11.30%; N, 1.82%.

Referential Example 7:
Synthesis of N-(3-hexadecyloxy-2-hydroxypropyl)-N-[2-O-(4-β-D-galactopyranosyl-β-D-glucopyranosyl)ethyl]hexadecanamide (Ie$_2$) [in the formula (Ie), R$^1$: C$_{15}$H$_{31}$, R$^{31}$: 4-O-β-D-galactopyranosyl-β-D-glucopyranosyl, R$^{32}$: H, R$^{51}$ : C$_{16}$H$_{33}$]:

(a) Synthesis of N-(2-acetoxy-3-hexadecyloxypropyl)-N-2-hydroxyethylhexadecanamide:

In a 30 ml four-necked flask equipped with a magnetic stirrer, dropping funnel, thermometer, reflux condenser and nitrogen inlet tube, 500 mg (0.595 mmol) of N-(3-hexadecyloxy-2-hydroxypropyl)-N-2-triphenylmethoxyhexadecanamide obtained in the step (b) of Referential Example 6 was dissolved in 10 ml of dry dichloromethane. To the resultant solution, 4 ml of pyridine and 2 ml of acetic anhydride were successively added dropwise over 30 minutes. The mixture was stirred for 8 hours at room temperature. After completion of the reaction, the reaction mixture was washed first with 2N hydrochloric acid and then with water. The reaction mixture was dried over salt cake and the solvent was then distilled off. The residue was purified by preparative thin-layer chromatography on silica gel, thereby obtaining 520 mg of N-(2-acetoxy-3-hexadecyloxypropyl)-N-2-triphenylmethoxyethylhexadecanamide. In a 10-ml two-necked flask, a 105 mg (0.119 mmol) portion of the compound was dissolved in 2 ml of dry dichloromethane, followed by an addition of 0.6 ml (0.505 mmol) of a 17% hexane solution of diethylaluminum chloride. After stirring the mixture for 40 minutes, a 5% aqueous sodium bicarbonate was added to terminate the reaction. A white insoluble matter thus formed was collected by filtration through Celite (trade mark), washed with water and then dried over salt cake. The solvent was distilled off. The residue was then purified by preparative thin-layer chromatography on silica gel to obtain 73 mg of the intended compound as colorless crystals (yield: 95%).

Melting point: 59.5°-60.0° C. IR (KBr, cm-1): 3514, 2920, 2854, 1713, 1641, 1473, 1386, 1275, 1224, 1206, 1146, 1077, 1050.
$^1$H-NMR (CDCl$_3$, δ): 0.88(6H,t), 1.2–1.8(54H,m), 2.07(3H,s), 2.38(2H,m), 3.3–3.9(11H,m), 5.1–5.3(1H,m).

(b) Synthesis of N-(3-hexadecyloxy-2-hydroxypropyl)-N-[2-O-(4-O-β-D-galactopyranosyl-β-D-glucopyranosyl)ethyl-]hexadecanamide (Ie$_2$) [In the formula (Ie), R$^1$: C$_{15}$H$_{31}$, R$^{31}$: 4-O-β-D-galactopyranosyl-β-D-glucopyranosyl, R$^{32}$: H, R$^{51}$: C$_{16}$H$_{33}$]:

In a 100 m; four-necked flask equipped with a mechanical stirrer, sealum cap, reflux condenser, thermometer and nitrogen inlet tube, 5.19 g (8.11 mmol) of N-(2-acetoxy-3-hexadecyloxypropyl)-N-2-hydroxyethyl hexadecanamide obtained in the above step (a) and 5.5 g (8.11 mmol) of β-D-lactose octaacetate prepared by a known process [Journal of American chemical Society, 47, 2052(1925)] were dissolved in 20 ml of dry dichloromethane, followed by an addition of 2.0 g of powdery molecular sieves 4A. The mixture was stirred at room temperature for 30 minutes under a nitrogen, to which 2.14 g (9.63 mmol) of trimethylsilyl triflate was added by a syringe. After stirring the resultant mixture for further 6 hours under the above conditions, the resultant suspension was filtered. The filtrate was washed first with a 5% aqueous sodium bicarbonate and then with water, and was thereafter dried over anhydrous sodium sulfate. The solvent was distilled off to obtain a crude product as a pale yellow oil. After dissolving the crude product in 50 ml of methanol, 14.1 g (73 mmol) of a 28% methanol solution of sodium methoxide was added dropwise at room temperature. The mixture was stirred for 3 hours. "Amberlyst 15" (trade name) was added to the reaction mixture to neutralize same. The "Amberlyst" was filtered off and the filtrate was concentrated to dryness. The resultant crude product as a pale yellow solid was purified by chromatography of a silica gel column (silica gel: 230–400 mesh, 300 g; solvent: chloroform/methanol=4/1), thereby obtaining 2.50 g of the title compound (Ie$_2$) as colorless powder (yield: 31.4%).

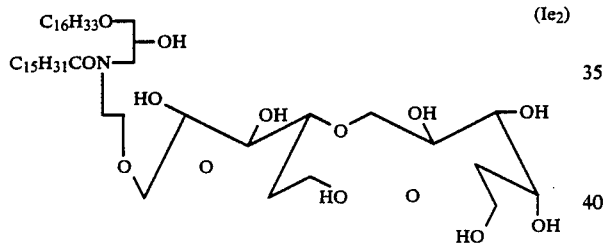

Melting point: 235° C. (decomposed).
IR (KBr, cm$^{-1}$): 3484, 3412, 1641, 1119, 1104, 1074, 1056, 1035.
$^1$H-NMR (DMSO-d$_6$/D$_2$O=9/1,50° C, δ):
0.849(6H,t,J=6.96Hz), 1.237(50H,s), 1.482(4H,br.s), 2.290(2H,m), 3.03–3.77 (22H,m), 4.19–4.97 (3H,m).
Elemental analysis: Calculated: C, 63.81% H, 10.38%; N, 1.52%, Found: C, 63.61%; H, 10.43%, N, 1.50%.

Referential Example 8:
Synthesis of N-(2-acetoxy-3-hexadecyloxypropyl)-N-[2-O-(2-acetmido-2-deoxy-β-D-glucopyranosyl)ethyl]hexadecanamide (Ie$_3$) [in the formula (Ie), R$^1$: C$_{15}$H$_{31}$, R$^{31}$: 2-acetamido-2-deoxy-β-D-glucopyranosyl, R$^{32}$:H, R$^{51}$: C$_{16}$H$_{33}$]:

(a) Synthesis of N-(2-acetoxy-3-hexadecyloxypropyl)-N-[2-O-(2-acetamido-3,4,6-tri-O-acetyl-2-deoxy-β-D-glucopyranosyl)ethyl]hexadecanamide:
In a 200 ml four-necked flask equipped with a mechanical stirrer, reflux condenser, thermometer and nitrogen inlet tube, 5.0 g (7.81 mmol) of N-(2-acetoxy-3-hexadecyloxypropyl)-N-2-hydroxyethylhexadecanamide obtained in the step (a) of Referential Example 7 and 7.0 g (21.3 mmol) of 2-methyl-(3,4,6-tri-O-acetyl-1,2-dideoxy-α-D-glucopyrano)-[2,1-d]-2-oxazoline prepared by a known process [Carbohydrate Research, 103, 286 (1982)] were dissolved in 120 ml of dry 1,2-dichloroethane. To the resultant solution, 1.3 g (5.17 mmol) of pyridinium p-toluenesulfonate was added. The mixture was heated under reflux for 24 hours. The reaction mixture was washed successively with a 5% aqueous sodium bicarbonate and water and was then dried over anhydrous sodium sulfate. The solvent was distilled off to obtain a crude product as a pale yellow oil. The crude product was purified by chromotagraphy on a silicon gel column (silica gel: 230–400 mesh, 600 g; solvent: ethyl acetate/hexane=4/1), thereby obtaining 4.93 g of the title compound as a colorless oil (yield: 69.8%).

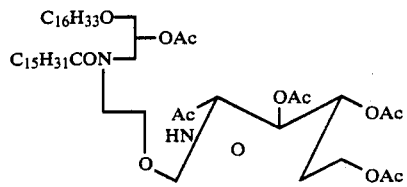

IR (liquid film, cm$^{-1}$): 3296, 1746, 1658, 1236, 1048.
$^1$H-NMR (CDCl$_3$, δ):
0.880(6H,t,J=2.93Hz), 1.256(50H,s), 1.566(4H,m), 1.923,1.932(3H,s,NHAc), 2.021(9H,s,OAc), 2.054,2061(3H,s,OAc), 2.086,2.091(3H,s,OAc), 3,405–4.29(13H,m), 4.590,4.625,4.659, 4.744(1H,each d,J=8.43Hz,1'-H), 5.024–4.251(3H,m,—CHAOc), 5.854,5.918, 5.952,5.986(1H, each d, J=8.43Hz,

—NHAc).

Elemental analysis: Calculated: C, 65.67%; H, 9.98%; N, 2.89%. Found: C, 65.56%; H, 9.91%; N, 2.76%.

(b) Synthesis of N-(2-acetoxy-3-hexadecyloxypropyl)-N-[2-O-(2-acetamido-2-deoxy-β-D-glucopyranosyl)ethyl]hexadecanamide (Ie$_3$) [In the formula (Ie), R$^1$: C$_{15}$H$_{31}$, R$^{31}$: 2-acetamido-2-deoxy-β-D-glucopyranosyl, R$^{32}$: H, R$^{51}$: C$_{16}$H$_{33}$]:

In a 100 ml of four-necked flask equipped with a magnetic stirrer, dropping funnel, reflux condenser, thermometer and nitrogen inlet tube, 4.30 g (4.44 mmol) of N-(2-acetoxy-3-hexadecyloxypropyl)-N-[2-O-(2-acetamido-3,4,6-tri-O-acetyl-2-deoxy-β-D-glucopyranosyl)ethyl]hexadecanamide obtained in the above step (a) was dissolved in 30 ml of dry dichloromethane, followed by a dropwise addition of 3.67 g (19.03 mmol) of a 28% methanol solution of sodium methoxide at room temperature under nitrogen. The mixture was stirred for 1 hour as was. After neutralizing the reaction mixture with 10 g of "Amberlyst 15", the "Amberlyst" was filtered off and the filtrate was concentrated. The residue was purified by column chromatography. The residue was purified by column chromotagraphy on a silica gel column (silica gel: 230–400 mesh, 150 g; solvent; chloroform/methanol=10/1), followed by recrystallization from a chloroform/acetone to obtain 2.45 g of the title compound (Ie$_3$) as colorless powder (yield: 68.6%).

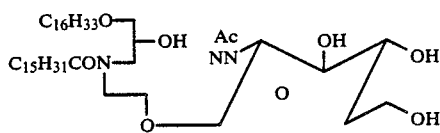
(Ie₃)

Melting point: 146.8°–148.8° C.

IR (KRb, cm⁻¹): 3428, 1624, 1112, 1080. ¹H-NMR (DMSO-d₆, δ):
0.854(6H,t), 1.237(50H,s), 1.470(4H,m), 1.798(3H,d,J=5.12Hz,—NHAc), 2.27(2H,m), 3.08–3.85(18H,m), 4.21–4.95(5H,m).

Elemental analysis: Calculated: C, 67.46%: H, 11.07%; N, 3.50%. Found: C, 67.08%; H, 11.00%; N, 3.31%.

Referential Example 9:

Synthesis of N-(3-hexadecyloxy-2-hydroxypropyl)-N-[2-O-(5-acetamido-3,5-dideoxy-α-D-glycero-β-D-galacto-2-nonuropyranosyl)ethyl]hexadecanamide (Ie₄) [in the formula (Ie), R¹: C₁₅H₃₁, R³¹: 5-acetamido-3,5-dideoxy-α-D-glycero-β-D-galacto-2-nonuropyranosyl, R³²: H, R⁵¹: C₁₆H₃₃]:

(a) Synthesis of N-(2-acetoxy-3-hexadecyloxypropyl)-N-[2-O-(methyl 5-acetmido-3,5-dideoxy-α-D-glycero-β-D-galacto-2-nonuropyranosonate)ethyl]hexadecanamide:

In a 50-ml four-necked flask, 2.86 g (4.48 mmol) of N-(2-acetoxy-3-hexadecyloxypropyl)-N-2-hydroethyl hexadecanamide prepared in the step (a) of Referential Example 7 and 1.90 g (3.73 mmol) of methyl 2-deoxy-2-chloro-4,7,8,9-tetra-O-acetyl-N-acetylneuraminate prepared by a known process [Chemische Berichte, 99, 611(1966); Chemical and Pharmaceutical Bulletin, 34, 2725(1986)] were dissolved in a mixed solvent of 5.0 ml of dry dichloromethane and 5.0 ml of dry toluene. At room temperature and under a nitrogen, 2.0 g of anhydrous calcium sulfate powder was added and the resultant mixture was stirred for 30 minutes. 1.54 g (5.60 mmol) of silver carbonate powder was added to the reaction mixture. After stirring the mixture at room temperature for further 3.5 hours, an insoluble matter was filtered off. The filtrate was concentrated under reduced pressure, and then purified by chromatography on a silica gel column (silica gel: 230–400 mesh, 300 g; solvent: ethyl acetate/hexane—3/1), thereby obtained 3.06 g of the title compound as a colorless oil (yield: 73.7%).

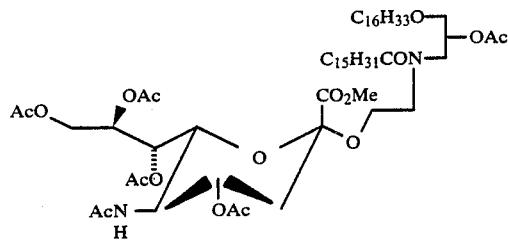

IR (liquid film, cm⁻¹): 3220, 1749, 1662, 1224, 1131, 1044.

¹H-NMR (CDCl₃, δ):
0.879(6H,t,J=6.59Hz), 1.257(50H,s), 1.569(4H,m), 1.881(3H,sHNAc), 2.025, 2.040, 2.049, 2.060, 2.121, 2.139, 2.156 (15H, each s,OAc), 2.34(2H,m), 2.564 (1H,dd,J=5.1 and 13.7Hz,3'-Heq), 3.409–4.16(13H,m), 3.778(3H,s,COOMe), 4.259(1H,m,9'-H), 4.86(1H,m,CHOCAc), 5.08–5.41-(4H,m,4'-H,7'-H,8'-H,NHAc).

Elemental analysis: Calculated: C, 63.64%; H, 9.41%; N, 2.52%. Found: C, 63.58%; H, 9.41%; N, 2.34%.

(b) Synthesis of N-(3-hexadecyloxy-2-hydroxypropyl)-N-[2-O-(5-acetamido-3,5-dideoxy-α-D-glycero-β-D-galacto-2-nonuropyranosyl)ethyl]hexadecanamide (Ie₄) [In the formula (Ie), R¹: C₁₅H₃₁, R³¹: 5-acetamido-3,5-dideoxy-β-D-glycero-β-D-galacto-2-nonuropyranosyl, R³²: H, R⁵¹: C₁₆H₃₃]:

In a 200 ml four-necked flask equipped with a mechanical stirrer, dropping funnel, reflux condenser, thermometer and nitrogen inlet tube, 2.10 g (1.89 mmol) of N-(2-acetoxy-3-hexadecyloxypropyl)-N-[2-O-(methyl 5-acetamido-3,5-dideoxy-α-D-glycero-β-D-galacto-2-nonuropyranosonate)ethyl]hexadecanamide prepared in the above step (a) was dissolved in 30 ml of dry pyridine, followed by an addition of 1.50 g (11.2 mmol) of lithium iodide. Under nitrogen, the reaction mixture was stirred for 4 hours under heat. Chloroform was added to the reaction mixture. The resultant mixture was washed successively with 2N hydrochloric acid and water, followed by separation of a chloroform solution. The chloroform solution was then dried over anhydrous sodium sulfate. The solvent was distilled off to obtain a pale-yellow oil. The crude oil was dissolved in 100 ml of dry dichloromethane, to which 2.2 g (11.4 mmol) of a 28% methanol solution of sodium methoxide was added dropwise at room temperature under nitrogen. The mixture was stirred for 3 hours. The reaction mixture was thereafter stirred for 3 hours together with 10 g of "Amberlyst 15" so as to neutralize same, and a solid matter was filtered off. The filtrate was concentrated and then purified by column chromatography on a silica gel column (silica gel: 230–400 mesh, 150 g; solvent: chloroform/methanol/water=100/40/1), thereby obtaining 1.209 g of the title compound (Ie₄) as colorless powder (yield: 75.7%).

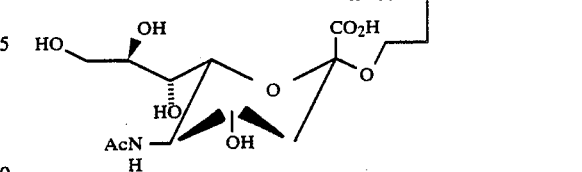
(Ie₄)

Melting point: 202° C. (decomposed).

IR (KBr, cm⁻¹): 3388, 1620, 1122, 1077, 1032.

¹H-NMR (DMSO-d₆/D₂O=100/1, 35° C., δ):
0.816(6H,br.s), 1.212(50H,br.s), 1.46(4H,br.s), 1.808,1.922(3H,each s,NHAc), 2.30(2H,m), 2.69(1H,m,3eq-H), 3.23–3.83(18H,m).

Elemental analysis: Calculated: C, 64.83%; H, 10.43%; N, 3.15%. Found: C, 64.83%; H, 10.50%; N, 3.02%.

EXAMPLE 1

Compounds Ia₁–Ia₁₈ prepared respectively in Referential Examples 1, 2 and 3 and following the procedures of these referential examples, compounds Ib₁–Ib₅ prepared respectively in Referential Example 4 and following the procedure of the referential example, compounds Id₁–Id₅ prepared respectively in Referential Example 5 and following the procedure of the referential example, compounds $Ie_1$–$Ie_4$ prepared respectively in Referential Examples 6–9, and conventional compounds $Ic_1$–$Ic_{13}$, $Ie_5$–$Ie_{14}$ and $II_1$–$II_{12}$ were used separately. Mixtures (Invention Products 1), each of which had been formulated by mixing vaseline and the compound (I or II) at a weight ratio of 3:1, and vaseline (Comparative Product 1) were evaluated in skin conductance and skin roughness by the following methods. Results will be summarized in Table 1.

(Testing methods)

Chosen as volunteers in winter were 10 women of 20–50 years of old who had skin roughness on their both cheeks. Different external skin care preparations were coated separately on the left and right cheeks of each volunteer for two weeks. On the following day of the the completion of the two-week coating test, tests were conducted with respect to the following properties.

(1) Skin conductance

After washing the face with warm water of 37° C., each volunteer was allowed to rest for 20 minutes in a room which was air-conditioned at 20° C. and 40% humidity. The water content of her horny layer was measured by a skin conductance meter (manufactured by IBS Company). A smaller conductance value indicates greater skin roughness. Conductance values of 5 and smaller indicate severe skin roughness. On the contrary, no substantial skin roughness is observed where this value is 20 or greater.

(2) Score of skin roughness

Skin roughness was observed visually and ranked in accordance with the following standard. Each score was indicated by an average value.

| Score | Ranking of skin roughness |
|---|---|
| 0 | No skin roughness was observed. |
| 1 | Slight skin roughness was observed. |
| 2 | Skin roughness was observed. |
| 3 | Rather severe skin roughness was observed. |
| 4 | Severe skin roughness was observed. |

TABLE 1-1

| Compound No. | Formula (Ia) $R^1$ | $R^{51}$ | A′ | Skin conductance | Score of skin roughness |
|---|---|---|---|---|---|
| Invention Product 1 | | | | | |
| $Ia_1$ | n-$C_{15}H_{31}$ | n-$C_{16}H_{33}$ | (—$CH_2$)$_3$OH | 20 | 1.1 |
| $Ia_2$ | n-$C_{15}H_{31}$ | n-$C_{16}H_{33}$ | (—$CH_2$)$_6$OH | 18 | 1.3 |
| $Ia_3$ | n-$C_9H_{19}$ | n-$C_{10}H_{21}$ | (—$CH_2$)$_3$OH | 10 | 1.5 |
| $Ia_4$ | n-$C_{17}H_{35}$ | n-$C_{10}H_{21}$ | (—$CH_2$)$_3$OH | 13 | 1.4 |
| $Ia_5$ | n-$C_9H_{19}$ | n-$C_{18}H_{37}$ | (—$CH_2$)$_3$OH | 17 | 1.2 |
| $Ia_6$ | n-$C_{17}H_{35}$ | n-$C_{18}H_{37}$ | (—$CH_2$)$_3$OH | 23 | 0.9 |
| $Ia_7$ | n-$C_{17}H_{35}$ | n-$C_{10}H_{21}$ | (—$CH_2$)$_6$OH | 11 | 1.5 |
| $Ia_8$ | n-$C_{10}H_{21}$ | n-$C_{18}H_{37}$ | (—$CH_2$)$_6$OH | 13 | 1.4 |
| $Ia_9$ | n-$C_{17}H_{35}$ | n-$C_{18}H_{37}$ | (—$CH_2$)$_6$OH | 20 | 1.1 |
| $Ia_{10}$ | n-$C_{15}H_{31}$ | n-$C_{16}H_{33}$ | —$CH_2CH(OH)CH_2OH$ | 22 | 0.9 |
| $Ia_{11}$ | n-$C_{17}H_{35}$ | n-$C_{10}H_{21}$ | —$CH_2CH(OH)CH_2OH$ | 19 | 1.0 |
| $Ia_{12}$ | n-$C_9H_{19}$ | n-$C_{18}H_{37}$ | —$CH_2CH(OH)CH_2OH$ | 18 | 1.1 |
| $Ia_{13}$ | n-$C_{17}H_{35}$ | n-$C_{18}H_{37}$ | —$CH_2CH(OH)CH_3$ | 13 | 1.3 |
| $Ia_{14}$ | n-$C_{17}H_{35}$ | n-$C_{18}H_{37}$ | —$C(CH_3)(CH_2OH)CH_2OH$ | 23 | 0.8 |
| $Ia_{15}$ | n-$C_{17}H_{35}$ | n-$C_{18}H_{37}$ | —$C(CH_3)_2CH_2OH$ | 13 | 1.3 |
| $Ia_{16}$ | n-$C_{17}H_{35}$ | n-$C_{18}H_{37}$ | —$CH(CH_3)CH_2OH$ | 15 | 1.2 |
| $Ia_{17}$ | n-$C_9H_{19}$ | n-$C_{14}H_{29}$ | —$C(CH_2OH)_3$ | 20 | 1.0 |

TABLE 1-2

| Compound No. | Formula (Ib) $R^1$ | $R^{51}$ | m′ | n′ | Skin conductance | Score of skin roughness |
|---|---|---|---|---|---|---|
| Invention Product 1 | | | | | | |
| $Ib_1$ | n-$C_{15}H_{31}$ | n-$C_{16}H_{33}$ | 2 | 0 | 20 | 1.0 |
| $Ib_2$ | n-$C_9H_{19}$ | n-$C_{10}H_{21}$ | 2 | 0 | 10 | 1.6 |
| $Ib_3$ | n-$C_9H_{19}$ | n-$C_{18}H_{37}$ | 2 | 0 | 14 | 1.5 |
| $Ib_4$ | n-$C_{17}H_{35}$ | n-$C_{10}H_{21}$ | 2 | 0 | 17 | 1.2 |
| $Ib_5$ | n-$C_{17}H_{35}$ | n-$C_{18}H_{37}$ | 2 | 0 | 23 | 0.9 |

TABLE 1-3

| Compound No. | Formula (Ic) $R^1$ | $R^2$ | $R^{52}$ | Y | W | Skin conductance | Score of skin roughness |
|---|---|---|---|---|---|---|---|
| Invention Product 1 | | | | | | | |
| $Ic_1$ | n-$C_{17}H_{35}$ | H | n-$C_{14}H_{29}$ | H | O | 14 | 1.5 |
| $Ic_2$ | n-$C_{17}H_{35}$ | H | n-$C_{14}H_{29}$ | Na | O | 15 | 1.4 |
| $Ic_3$ | n-$C_{17}H_{35}$ | H | n-$C_{14}H_{29}$ | H | $CH_2$ | 11 | 1.7 |
| $Ic_4$ | n-$C_{17}H_{35}$ | H | n-$C_{14}H_{29}$ | Na | $CH_2$ | 13 | 1.4 |
| $Ic_5$ | n-$C_{15}H_{31}$ | $CH_3$ | n-$C_{16}H_{33}$ | K | O | 13 | 1.4 |
| $Ic_6$ | n-$C_{15}H_{31}$ | $PhCH_2$ | n-$C_{16}H_{33}$ | K | O | 12 | 1.6 |
| $Ic_7$ | n-$C_{15}H_{31}$ | $(CH_3)_2CH$ | n-$C_{16}H_{33}$ | K | O | 15 | 1.4 |
| $Ic_8$ | n-$C_{15}H_{31}$ | $HOCH_2$ | n-$C_{16}H_{33}$ | K | O | 18 | 1.2 |
| $Ic_9$ | n-$C_{15}H_{31}$ | $CH_3SCH_2CH_2$ | n-$C_{16}H_{33}$ | K | O | 16 | 1.3 |
| $Ic_{10}$ | n-$C_{15}H_{31}$ | $YOCOCH_2$ | n-$C_{16}H_{33}$ | H | O | 15 | 1.4 |
| $Ic_{11}$ | n-$C_{15}H_{31}$ | $YOCOCH_2CH_2$ | n-$C_{16}H_{33}$ | H | O | 13 | 1.5 |
| $Ic_{12}$ | n-$C_{15}H_{31}$ | 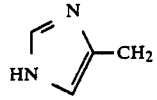 | n-$C_{16}H_{33}$ | K | O | 11 | 1.8 |

TABLE 1-3-continued

| Compound No. | Formula (Ic) R$^1$ | R$^2$ | R$^{52}$ | Y | W | Skin conductance | Score of skin roughness |
|---|---|---|---|---|---|---|---|
| Ic$_{13}$ | n-C$_{15}$H$_{31}$ |  | n-C$_{16}$H$_{33}$ | K | O | 10 | 1.9 |

TABLE 1-4

| Compound No. | Formula (Id) R$^1$ | R$^{53}$ | Skin conductance | Score of skin roughness |
|---|---|---|---|---|
| Invention Product 1 | | | | |
| Id$_1$ | n-C$_{17}$H$_{35}$ | n-C$_{14}$H$_{29}$ | 21 | 1.0 |
| Id$_2$ | n-C$_9$H$_{19}$ | n-C$_{16}$H$_{33}$ | 18 | 1.1 |

TABLE 1-4-continued

| Compound No. | Formula (Id) R$^1$ | R$^{53}$ | Skin conductance | Score of skin roughness |
|---|---|---|---|---|
| Id$_3$ | n-C$_9$H$_{19}$ | n-C$_{10}$H$_{21}$ | 13 | 1.3 |
| Id$_4$ | n-C$_{17}$H$_{35}$ | n-C$_{10}$H$_{21}$ | 17 | 1.1 |
| Id$_5$ | cis-9-C$_{17}$H$_{33}$ | n-C$_{16}$H$_{33}$ | 25 | 0.8 |

TABLE 1-5

| Compound No. | Formula (Ie) R$^1$ | R$^{51}$ | R$^{31}$ | R$^{32}$ | Skin conductance | Score of skin roughness |
|---|---|---|---|---|---|---|
| Invention Product 1 | | | | | | |
| Ie$_1$ | n-C$_{15}$H$_{31}$ | n-C$_{16}$H$_{33}$ | Glucopyranosyl | H | 25 | 1.0 |
| Ie$_2$ | n-C$_{15}$H$_{31}$ | n-C$_{16}$H$_{33}$ | 4-O-β-D-Galactopyranosyl-β-D-glucopyranosyl | H | 29 | 0.8 |
| Ie$_3$ | n-C$_{15}$H$_{31}$ | n-C$_{16}$H$_{33}$ | 2-Acetoamido-2-deoxy-β-D-glucopyranosyl | H | 31 | 0.7 |
| Ie$_4$ | n-C$_{15}$H$_{31}$ | n-C$_{16}$H$_{33}$ | 5-Acetamido-3,5-dideoxy-α-D-glycero-β-D-galacto-2-nonuropyranosyl | H | 33 | 0.5 |
| Ie$_5$ | n-C$_{15}$H$_{31}$ | n-C$_{16}$H$_{33}$ | $-\overset{O}{\underset{O^\ominus}{\overset{\|}{P}}}-OCH_2CH_2-\overset{\oplus}{N}H_3$ | H | 15 | 1.5 |
| Ie$_6$ | n-C$_{15}$H$_{31}$ | n-C$_{16}$H$_{33}$ | $-\overset{O}{\underset{O^\ominus}{\overset{\|}{P}}}-OCH_2CH_2-\overset{\oplus}{N}H_2(CH_3)$ | H | 16 | 1.2 |
| Ie$_5$ | n-C$_{15}$H$_{31}$ | n-C$_{16}$H$_{33}$ | $-\overset{O}{\underset{O^\ominus}{\overset{\|}{P}}}-OCH_2CH_2-\overset{\oplus}{N}(CH_3)_3$ | H | 18 | 1.2 |

TABLE 1-6

| Compound No. | Formula (Ie) R$^1$ | R$^{51}$ | R$^{31}$ | R$^{32}$ | Skin conductance | Score of skin roughness |
|---|---|---|---|---|---|---|
| Invention Product 1 | | | | | | |
| Ie$_8$ | n-C$_{15}$H$_{31}$ | n-C$_{16}$H$_{33}$ | $-\overset{O}{\underset{O^\ominus}{\overset{\|}{P}}}-OCH_2CH_2-\overset{\oplus}{N}H_2(CH_2C_6H_5)$ | H | 15 | 1.4 |
| Ie$_9$ | n-C$_{17}$H$_{35}$ | n-C$_{14}$H$_{29}$ | $-\overset{O}{\underset{O^\ominus}{\overset{\|}{P}}}-OCH_2CH_2-\overset{\oplus}{N}(C_2H_5)_3$ | H | 18 | 1.1 |

TABLE 1-6-continued

| Compound No. | Formula (Ie) R¹ | R⁵¹ | R³¹ | R³² | Skin conductance | Score of skin roughness |
|---|---|---|---|---|---|---|
| $Ie_{10}$ | n-$C_9H_{19}$ | n-$C_{10}H_{21}$ | $-\overset{O}{\underset{O^{\ominus}}{\overset{\|}{P}}}-OCH_2CH_2-\overset{\oplus}{\underset{(CH_2)_2-Ph}{NH_2}}$ | H | 11 | 1.8 |
| $Ie_{11}$ | i-$C_{17}H_{35}$ | i-$C_{18}H_{37}$ | $-\overset{O}{\underset{O^{\ominus}}{\overset{\|}{P}}}-OCH_2CH_2-\overset{\oplus}{N(CH_3)_3}$ | H | 16 | 1.3 |
| $Ie_{12}$ | n-$C_{17}H_{35}$ | Oleyl | $-\overset{O}{\underset{O^{\ominus}}{\overset{\|}{P}}}-OCH_2CH_2-\overset{\oplus}{N(CH_3)_3}$ | H | 13 | 1.6 |
| $Ie_{13}$ | n-$C_{15}H_{31}$ | n-$C_{16}H_{33}$ | H | $-\overset{O}{\underset{O^{\ominus}}{\overset{\|}{P}}}-OCH_2CH_2-\overset{\oplus}{N(CH_3)_3}$ | 11 | 1.7 |
| $Ie_{14}$ | n-$C_{15}H_{31}$ | n-$C_{16}H_{33}$ | $-\overset{O}{\underset{O^{\ominus}}{\overset{\|}{P}}}-OCH_2CH_2-\overset{\oplus}{N(CH_3)_3}$ | $-\overset{O}{\underset{O^{\ominus}}{\overset{\|}{P}}}-OCH_2CH_2-\overset{\oplus}{N(CH_3)_3}$ | 10 | 1.9 |

TABLE 1-7

| Compound No. | Formula (II) R⁶ | R⁷ | R⁸ | Skin conductance | Score of skin roughness |
|---|---|---|---|---|---|
| Invention Product 1 | | | | | |
| $II_1$ | n-$C_{16}H_{33}$ | n-$C_{16}H_{33}$ | $-CH_2CH_2OH$ | 18 | 1.0 |
| $II_2$ | n-$C_{10}H_{21}$ | n-$C_{10}H_{21}$ | $-CH_2CH_2OH$ | 8 | 1.6 |
| $II_3$ | n-$C_{10}H_{21}$ | n-$C_{18}H_{37}$ | $-CH_2CH_2OH$ | 11 | 1.4 |
| $II_4$ | n-$C_{18}H_{37}$ | n-$C_{18}H_{37}$ | $-CH_2CH_2OH$ | 21 | 0.9 |
| $II_5$ | n-$C_{16}H_{33}$ | n-$C_{16}H_{33}$ | $-CH_2CH_2OH$ | 17 | 1.0 |
| $II_6$ | n-$C_{10}H_{21}$ | n-$C_{10}H_{21}$ | $-CH_2COOH$ | 7 | 1.5 |
| $II_7$ | n-$C_{10}H_{21}$ | n-$C_{18}H_{37}$ | $-CH_2COOH$ | 10 | 1.3 |
| $II_8$ | n-$C_{18}H_{37}$ | n-$C_{18}H_{37}$ | $-CH_2COOH$ | 20 | 0.9 |
| $II_9$ | n-$C_{16}H_{33}$ | n-$C_{16}H_{33}$ | $-CH_2COOH$ | 17 | 1.1 |
| $II_{10}$ | n-$C_{10}H_{21}$ | n-$C_{10}H_{21}$ | $-COCH_3$ | 9 | 1.7 |
| $II_{11}$ | n-$C_{10}H_{21}$ | n-$C_{18}H_{37}$ | $-COCH_3$ | 12 | 1.5 |
| $II_{12}$ | n-$C_{18}H_{37}$ | n-$C_{18}H_{37}$ | $-COCH_3$ | 20 | 1.0 |
| Comparative Product 1 | | | | 6 | 2.8 |

Example 2

Using separately the compounds used in Example 1, external skin care preparations (emulsified cosmetic preparations) of their corresponding compositions shown below in Table 2 were formulated. Their effects for the improvement of skin roughness were evaluated in the same manner as in Example 1. Results are shown in Table 3.

TABLE 2

| Emulsified cosmetic preparation Composition | Invention product | | | Comparative product | | | (wt. %) |
|---|---|---|---|---|---|---|---|
| | 2 | 3 | 4 | 2 | 3 | 4 | |
| Glyceryl ether [in formula (VII), R is represented by formula (VIII)] | 2.0 | — | — | 2.0 | — | — | |
| Arginine monocetylphosphate | — | 2.0 | — | — | 2.0 | — | |
| Polyoxyethylene (20) sorbitan stearate | — | — | 1.0 | — | — | 1.0 | |
| Sorbitan monostearate | — | — | 1.0 | — | — | 1.0 | |
| 2-Octyldodecyl myristate | 10.0 | 10.0 | 10.0 | 10.0 | 10.0 | 10.0 | |
| Vaseline | 3.0 | 3.0 | 3.0 | 3.0 | 3.0 | 3.0 | |
| Squalane | 5.0 | 5.0 | 5.0 | 5.0 | 5.0 | 5.0 | |
| Tocopherol acetate | 0.5 | 0.5 | 0.5 | 0.5 | 0.5 | 0.5 | |
| Compound (I or II) | 1.0 | 1.0 | 1.0 | — | — | — | |

TABLE 2-continued

| Emulsified cosmetic preparation | Invention product | | | Comparative product | | | (wt. %) |
|---|---|---|---|---|---|---|---|
| Composition | 2 | 3 | 4 | 2 | 3 | 4 | |
| Water | Balance | Balance | Balance | Balance | Balance | Balance | |

TABLE 3-1

| | Score of skin roughness | | |
|---|---|---|---|
| | 2 | 3 | 4 |
| Invention product | | | |
| Compound $Ia_1$ | 0.2 | 0.4 | 0.8 |
| Compound $Ia_2$ | 0.3 | 0.5 | 1.0 |
| Compound $Ia_3$ | 0.7 | 1.0 | 1.3 |
| Compound $Ia_3$ | 0.7 | 1.0 | 1.3 |
| Compound $Ia_4$ | 0.5 | 0.7 | 1.1 |
| Compound $Ia_5$ | 0.3 | 0.5 | 1.0 |
| Compound $Ia_6$ | 0.1 | 0.3 | 0.7 |
| Compound $Ia_7$ | 0.6 | 0.9 | 1.2 |
| Compound $Ia_8$ | 0.5 | 0.7 | 1.1 |
| Compound $Ia_9$ | 0.2 | 0.4 | 0.9 |
| Compound $Ia_{10}$ | 0.1 | 0.3 | 0.6 |
| Compound $Ia_{11}$ | 0.3 | 0.5 | 0.8 |
| Compound $Ia_{12}$ | 0.3 | 0.5 | 0.9 |
| Compound $Ia_{13}$ | 0.5 | 0.7 | 1.1 |
| Compound $Ia_{14}$ | 0.1 | 0.3 | 0.6 |
| Compound $Ia_{15}$ | 0.5 | 0.7 | 1.0 |
| Compound $Ia_{16}$ | 0.4 | 0.6 | 0.9 |
| Compound $Ia_{17}$ | 0.2 | 0.4 | 0.7 |
| Compound $Ib_1$ | 0.1 | 0.2 | 0.7 |
| Compound $Ib_2$ | 0.8 | 1.0 | 1.2 |
| Compound $Ib_3$ | 0.6 | 0.9 | 1.1 |
| Compound $Ib_4$ | 0.4 | 0.6 | 0.9 |
| Compound $Ib_5$ | 0.2 | 0.4 | 0.8 |

TABLE 3-2

| | Score of skin roughness | | |
|---|---|---|---|
| | 2 | 3 | 4 |
| Invention product | | | |
| Compound $Ic_1$ | 0.7 | 0.9 | 1.2 |
| Compound $Ic_2$ | 0.6 | 0.8 | 1.1 |
| Compound $Ic_3$ | 1.0 | 1.3 | 1.6 |
| Compound $Ic_4$ | 0.8 | 1.0 | 1.3 |
| Compound $Ic_5$ | 0.8 | 1.0 | 1.3 |
| Compound $Ic_6$ | 0.9 | 1.2 | 1.5 |
| Compound $Ic_7$ | 0.6 | 0.8 | 1.1 |
| Compound $Ic_8$ | 0.4 | 0.6 | 0.9 |
| Compound $Ic_9$ | 0.5 | 0.7 | 1.0 |
| Compound $Ic_{10}$ | 0.6 | 0.8 | 1.1 |
| Compound $Ic_{11}$ | 0.8 | 1.0 | 1.3 |
| Compound $Ic_{12}$ | 1.0 | 1.3 | 1.6 |
| Compound $Ic_{13}$ | 1.1 | 1.4 | 1.7 |
| Compound $Id_1$ | 0.2 | 0.4 | 0.7 |
| Compound $Id_2$ | 0.3 | 0.5 | 0.8 |
| Compound $Id_3$ | 0.5 | 0.8 | 1.1 |
| Compound $Id_4$ | 0.3 | 0.5 | 0.8 |
| Compound $Id_5$ | 0.1 | 0.3 | 0.6 |

TABLE 3-3

| | Score of skin roughness | | |
|---|---|---|---|
| | 2 | 3 | 4 |
| Invention product | | | |
| Compound $Ie_1$ | 0.4 | 0.6 | 0.9 |
| Compound $Ie_2$ | 0.4 | 0.5 | 0.8 |
| Compound $Ie_3$ | 0.3 | 0.4 | 0.7 |
| Compound $Ie_4$ | 0.2 | 0.2 | 0.4 |
| Compound $Ie_5$ | 0.7 | 0.9 | 1.2 |
| Compound $Ie_6$ | 0.8 | 0.9 | 1.4 |
| Compound $Ie_7$ | 0.5 | 0.7 | 1.0 |
| Compound $Ie_8$ | 0.6 | 1.1 | 1.3 |
| Compound $Ie_9$ | 0.6 | 0.6 | 1.0 |
| Compound $Ie_{10}$ | 1.0 | 1.2 | 1.8 |
| Compound $Ie_{11}$ | 0.7 | 0.8 | 1.1 |
| Compound $Ie_{12}$ | 0.9 | 0.9 | 1.5 |

TABLE 3-3-continued

| | Score of skin roughness | | |
|---|---|---|---|
| | 2 | 3 | 4 |
| Compound $Ie_{13}$ | 0.9 | 1.1 | 1.5 |
| Compound $Ie_{14}$ | 1.2 | 1.4 | 1.9 |

TABLE 3-4

| | Score of skin roughness | | |
|---|---|---|---|
| | 2 | 3 | 4 |
| Invention product | | | |
| Compound $II_1$ | 0.1 | 0.3 | 0.8 |
| Compound $II_2$ | 0.8 | 1.0 | 1.2 |
| Compound $II_3$ | 0.5 | 0.8 | 1.1 |
| Compound $II_4$ | 0.1 | 0.3 | 0.7 |
| Compound $II_5$ | 0.2 | 0.4 | 0.8 |
| Compound $II_6$ | 0.8 | 1.0 | 1.2 |
| Compound $II_7$ | 0.5 | 0.8 | 1.1 |
| Compound $II_8$ | 0.2 | 0.4 | 0.8 |
| Compound $II_9$ | 0.1 | 0.3 | 0.9 |
| Compound $II_{10}$ | 0.8 | 1.1 | 1.2 |
| Compound $II_{11}$ | 0.4 | 0.8 | 1.2 |
| Compound $II_{12}$ | 0.2 | 0.4 | 0.8 |
| Comparative product | 2.1 | 2.5 | 2.6 |

Example 3: Cosmetic Emulsion

A cosmetic emulsion was formulated in accordance with the below-described composition. The water-phase components were maintained at 70° C. while mixing them under heat. On the side, the oil-phase components were heated and mixed at 80° C. After adding the above-mentioned water-phase components gradually under stirring to the oil-phase components, the resultant mixture was emulsified uniformly by a homomixer. Subsequent to the emulsification, the mixture was cooled down to 30° C. by a heat exchanger to obtain the cosmetic emulsion.

| | (wt. %) |
|---|---|
| Oil-phase components: | |
| Compound $II_1$ | 1.0 |
| Microcrystalline wax | 0.5 |
| Bees wax | 2.0 |
| Lanolin | 1.5 |
| Liquid paraffin | 30.0 |
| Sorbitan sesquioleate | 4.0 |
| Polyoxyethylenesorbitan monooleate (20 E.O.) | 1.0 |
| Aluminum stearate | 0.2 |
| Butyl paraben | 0.1 |
| Water-phase components: | |
| Glycerin | 8.0 |
| Methyl paraben | 0.3 |
| Perfume base | 0.1 |
| Purified water | Balance |

Example 4: Cleansing Cream

A cleansing creams was formulated in accordance with the below-described composition. The oil-phase components were maintained at 80° C. while mixing them under heat. The water-phase components which had been heated and mixed at 70° C. on the side were added to the above-mentioned oil-phase components, and the resultant mixture was then emulsified uniformly by a homogenizer. Subsequent to the emulsification, the mixture was cooled down to 30° C. by a heat exchanger to obtain the cleansing cream.

| | (wt. %) |
|---|---|
| Oil-phase components: | |
| Compound II$_1$ | 3.0 |
| Paraffin | 2.0 |
| Cetanol | 1.0 |
| Vaseline | 18.5 |
| Liquid paraffin | 28.0 |
| Glycerin monostearate polyoxyethylene monolaurate (20 E.O.) | 3.0 |
| Water-phase components: | |
| Propylene glycol | 3.0 |
| Glycerin | 2.0 |
| Methyl paraben | 0.3 |
| Perfume base | 0.1 |
| Purified water | Balance |

Example 5: Toilet Water

A toilet water was formulated in accordance with the below-described composition. Glycerin and propylene glycol were added to purified water. The former components were dissolved in the latter at room temperature to obtain a purified water portion. On the other hand, emollient and the surfactant, antiseptic and perfume base were added to the ethanol, and the former component were dissolved in the latter at room temperature. The thus-formed solution was added to the above-mentioned purified water portion to solubilize the former. The resultant solution was modified in color with a dye and then filtered to obtain the toilet water.

| | | (wt. %) |
|---|---|---|
| Moisturizers: | Glycerin | 5.0 |
| | Propylene glycol | 4.0 |
| Emollient: | Compound II$_2$ | 0.1 |
| Surfactant: | Polyoxyethylene hydrogenated castor oil (40 E.O.) | 1.0 |
| Ethanol | | 10.0 |
| Antiseptic: | Methyl paraben | 0.2 |
| Purified water | | Balance |

Example 6: Lip Stick

A lip stick was prepared in accordance with the below-described composition. Base materials were heated and molten, and were then mixed uniformly. A color was added to the melt. After kneading the resultant mixture and dispersing the color evenly, the mixture was molten again and a perfume base was added. The melt was defoamed and poured into a mold. The mold was cooled quickly to solidify the melt. The thus-solidified stick was taken out of the mold and filled in a dispenser. After straightening up the external appearance of the stick further, it was caused to pass through a flame (flaming) whereby its surface was rendered uniform to obtain the lip stick.

| | (wt. %) |
|---|---|
| Base materials: | |
| Compound II$_3$ | 5.0 |
| Castor oil | 45.0 |
| Hexadecyl alcohol | 23.0 |
| Lanolin | 4.0 |
| Bees wax | 5.0 |
| Ozocerite | 4.0 |
| Candelilla wax | 4.0 |
| Carnauba wax | 2.0 |
| Tocopherol | 0.1 |
| Butyl paraben | 0.1 |
| Colors: | |
| Titanium oxide | 2.0 |
| Red Color No. 202 | 0.5 |
| Red Color No. 204 | 2.5 |
| Red Color No. 227 (Al rake) | 2.5 |
| Orange Color No. 201 | 0.2 |
| Perfume base | 0.1 |

Example 7: Emulsion-Type Foundation

An emulsion-type foundation was formulated in accordance with the below-described composition. The oil-phase components were mixed, heated and molten, and maintained at 80° C. On the other hand, the powdery components were added to and dispersed in the water-phase components. The resultant dispersion was heated to 70° C. The above oil-phase components were added to the water-phase components, followed by emulsification and dispersion by an emulsifying machine. An emulsion thus obtained was cooled down to 30° C. by a heat exchanger to obtain the emulsion-type foundation.

| | (wt. %) |
|---|---|
| Oil-phase components: | |
| Compound II$_4$ | 3.0 |
| Stearic acid | 5.0 |
| Cetostearyl alcohol | 1.0 |
| Jojoba oil | 15.0 |
| Glycerin monostearate | 2.0 |
| Propylene glycol monolaurate | 3.0 |
| Water-phase components: | |
| Propylene glycol | 4.0 |
| Triethanolamine | 1.2 |
| Methyl paraben | 0.3 |
| Perfume base | 0.1 |
| Purified water | Balance |
| Powdery components: | |
| Titanium oxide | 8.0 |
| Talc | 4.0 |
| Iron oxide | 0.5 |

Example 8: Hair Tonic

A hair tonic was formulated in accordance with the below-described composition.

| | (wt. %) |
|---|---|
| Compound II$_2$ | 0.2 |
| Menthol | 0.2 |
| Pilocton auramine (antidandruff agent) | 0.1 |
| Methyl nicotinate | 0.1 |
| Ethanol | 50.0 |
| Purified water | Balance |

Example 9

A cosmetic emulsion was obtained in the same manner as in Example 3 except that Compound $II_9$ was used in place of Compound $II_1$.

Example 10

A cleansing cream was obtained in the same manner as in Example 4 except that Compound $II_9$ was used instead of Compound $II_1$.

Example 11

A toilet water was obtained in the same manner as in Example 5 except that Compound $II_{10}$ was used in lieu of Compound $II_2$.

Example 12

A lip stick was obtained in the same manner as in Example 6 except that Compound $II_{11}$ was used in lieu of Compound $II_3$.

Example 13

An emulsion-type foundation was obtained in the same manner as in Example 7 except that Compound $II_{12}$ was used instead of Compound $II_4$.

Example 14

A hair tonic was obtained in the same manner as in Example 8 except that Compound $II_{10}$ was used in lieu of Compound $II_2$.

Example 15: Cosmetic Emulsion

In accordance with the below-described composition, the oil-phase components were mixed, heated and molten, and maintained at 70° C. The water-phase components were also mixed, heated and molten at 70° C. The above oil-phase components were added to the water-phase components, followed by emulsification by an emulsifying machine. An emulsion thus obtained was cooled down to a final temperature of 30° C. by a heat exchanger to obtain a cosmetic emulsion.

|  | (wt. %) |
|---|---|
| Oil-phase components: | |
| Cetanol | 0.5 |
| Vaseline | 3.0 |
| Compound $II_5$ | 5.0 |
| Polyoxyethylene (10) monooleate | 2.0 |
| Stearic acid | 2.0 |
| Water-phase components: | |
| 1,3-Butylene glycol | 3.0 |
| Dipropylene glycol | 6.0 |
| Triethanolamine | 1.0 |
| Ethyl paraben | 0.1 |
| Methyl paraben | 0.2 |
| Perfume base | 0.1 |
| Purified water | Balance |

Example 16: Emulsion-Type Foundation

In accordance with the below-described composition, the oil-phase components were mixed, heated and molten, and maintained at 70° C. On the other hand, the powdery components were added to and dispersed in the water-phase components. The resultant dispersion was heated to 70° C. The above oil-phase components were added to the water-phase components, followed by emulsification and dispersion by an emulsifying machine. An emulsion thus obtained was cooled down to a final temperature of 30° C. by a heat exchanger and was then filled in a container, whereby the emulsion-type foundation was obtained.

|  | (wt. %) |
|---|---|
| Oil-phase components: | |
| Stearic acid | 5.0 |
| Cetostearyl alcohol | 1.0 |
| Olive oil | 15.0 |
| Compound $II_5$ | 3.0 |
| Glycerin monostearate | 2.0 |
| Propylene glycol monolaurate | 3.0 |
| Water-phase components: | |
| Propylene glycol | 4.0 |
| Triethanolamine | 1.2 |
| Ethyl paraben | 0.1 |
| Methyl paraben | 0.2 |
| Perfume base | 0.1 |
| Purified water | Balance |
| Powdery components: | |
| Titanium oxide | 8.0 |
| Talc | 4.0 |
| Iron oxide | 0.5 |

Example 17: Lip Stick

In accordance with the below-described composition, a lip stick was obtained by heating and melting microcrystalline wax, candelilla wax, castor oil, Compound $II_5$, jojoba oil, olive oil and lanolin at 90°–100° C., adding the pigment to the melt, stirring the resultant mixture to disperse the pigment, deaerating the the thus-pigmented mixture, adding the perfume base to the thus-deaerated mixture, pouring it into a stick mold, cooling the mold to 15°–20° C. and then taking the resultant lip stick out of the mold.

|  | (wt. %) |
|---|---|
| Microcrystalline wax | 6.0 |
| Candelilla wax | 3.0 |
| Castor oil | 40.0 |
| Compound $II_5$ | 8.0 |
| Jojoba oil | 6.0 |
| Lanolin | 10.0 |
| Olive oil | Balance |
| Pigment | 7.0 |
| Perfume base | 0.1 |

Example 18: W/O Type Massage Cream

In accordance with the below-described composition, soap powder was added to purified water, and the resultant mixture was heated to and maintained at 70° C. The oil-phase components were mixed, and then heated to and maintained at 70° C. The above water-phase portion was added to the oil-phase portion, followed by provisional emulsification. The resultant mixture was thereafter emulsified evenly by a homomixer, followed by cooling to room temperature or so by a heat exchanger.

|  | (wt. %) |
|---|---|
| Oil-phase components: | |
| Paraffin | 4.0 |
| Microcrystalline wax | 6.0 |
| Bees wax | 6.0 |
| Vaseline | 10.0 |
| Compound $II_8$ | 4.0 |
| Liquid paraffin | 40.0 |
| Sorbitan sesquioleate | 3.5 |

-continued

| | (wt. %) |
|---|---|
| Polyoxyethylene sorbitan monooleate (20 E.O.) | 0.5 |
| Water-phase components: | |
| Ethyl paraben | 0.1 |
| Methyl paraben | 0.2 |
| Tocopheryl acetate | 0.5 |
| Soap powder | 0.3 |
| Purified water | Balance |

Example 19: Pack (Peel-Off Type)

In accordance with the below-described composition, the water-phase components were mixed, heated and molten, and maintained at 70° C. Similarly, the oil-phase components were heated to and mixed at 70° C. The oil-phase components were added to the above water-phase components, and the resultant mixture was emulsified by an emulsifying machine. The powdery components and film-forming agent were added to and mixed with the emulsion. The resultant emulsion was cooled down to a final temperature of 30° C. by a heat exchanger and then filled in a container, whereby a pack was obtained.

| | (wt. %) |
|---|---|
| Oil-phase components: | |
| Squalane | 2.0 |
| Compound II$_6$ | 1.0 |
| Hydrophobic glycerin monostearate polyoxyethylene sorbitan monolaurate (20 E.O.) | 1.0 |
| Water-phase components: | |
| Glycerin | 3.0 |
| Propylene glycol | 3.0 |
| Veegum | 1.0 |
| Purified water | Balance |
| Ethanol | 7.0 |
| Powdery components: | |
| Titanium oxide | 10.0 |
| Kaolin | 3.0 |
| Film-forming agent: | |
| Polyvinyl alcohol | 10.0 |
| Perfume base | 0.5 |
| Antiseptic | 0.1 |

Example 20: Hair Tonic

The following components were heated to and dissolved at 70° C., and were then cooled to obtain a hair tonic.

| | (wt. %) |
|---|---|
| Compound II$_7$ | 0.2 |
| Menthol | 0.2 |
| Pilocton auramine (antidandruff agent) | 0.1 |
| Methyl nicotinate | 0.1 |
| Ethanol | 45.0 |
| Purified water | Balance |

All the external skin care preparations obtained in Examples 3–20 were highly effective for the improvement of skin roughness and exhibited superb moistening ability.

We claim:

1. An external skin care preparation comprising (a) a compound represented by Formula (I), or a salt thereof:

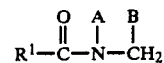

wherein R$^1$ means an aliphatic hydrocarbon group having 9–25 carbon atoms, A denotes a group ${-}(CH_2)_l OH$ (1: integer of 3;14 5), a group

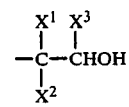

(X$^1$,X$^2$,X$^3$: H, C$_{1-5}$-alkyl or hydroxyalkyl, individually), a group $CH_2CH_2O)_m H$ (m: integer of at least 2), a group

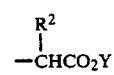

(Y: H or alkali metal; R$^2$: H, —CH$_3$,

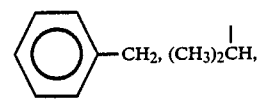

(CH$_3$)$_2$CHCH$_2$—, C$_2$H$_5$(CH$_3$CHCH$_2$—, HOCH$_2$—, CH$_3$(HO)CH—, CH$_3$SCH$_2$CH$_2$—, YOCOCH$_2$—, YOCOCH$_2$CH$_2$—,

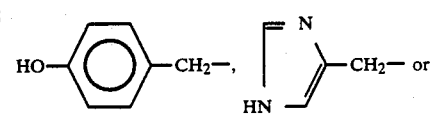

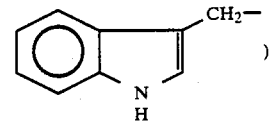

or a group —CH$_2$CH$_2$OR$^2$[R$^3$: sugar residuum or group

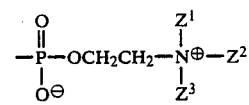

(Z$^1$, Z$^2$, Z$^3$: H, straight-chain or branched X$_{1-6}$-alkyl, or aralkyl)], and B stands for a group

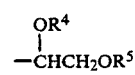

[R$^4$: H, sugar residuum, group

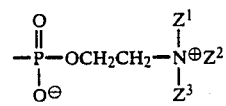

($Z^1, Z^2, Z^3$: the defined above) or group $+CH_2CH_2O)_nH$ (n: integer of at least 1); $R^5$: $C_{8-28}$-aliphatic hydrocarbon group] or a group

$R^5$: as defined above), with a proviso that $X^1, X^2, X^3$ and $R^4$ do not mean H at the same time, and (b) at least one member selected from the group consisting of a surfactant, a plant oil, an animal oil, a synthetic oil, a fatty acid, a glyceride, an analgesic, an antiphlogistic, and antipruritic, a disinfectant, an astringent, an emollient, a hormone, a moisturizer, an ultraviolet absorbent, an alcohol, a chelating agent, a pH regulator, an antiseptic, a thickener, a pigment, and a perfume.

2. The external skin care preparation as claimed in claim 1, wherein the compound (I) is represented by the following formula (Ia):

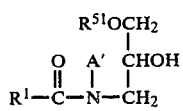

wherein $R^1$ has the same meaning as defined above, $R^{51}$ denotes an aliphatic hydrocarbon group having 10–26 carbon atoms, and A' is a group $+CH_2)_lOH$ (l: as defined above) or

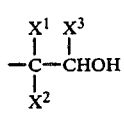

($X^1, X^2, X^3$: as defined above, with a proviso that $X^1, X^2$ and $X^3$ do not mean H at the same time).

3. The external skin care preparation as claimed in claim 1, wherein the compound (I) is represented by the following formula (Ib):

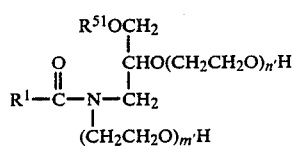

wherein $R^1$ has the same meaning as defined above, $R^{51}$ denotes an aliphatic hydrocarbon group having 10–26 carbon atoms, m' is an integer of at least 1, and n' stands for an integer of at least 0, with a proviso that m' and n' do not mean 1 and 0 respectively at the same time.

4. The external skin care preparation as claimed in claim 1, wherein the compound (I) is represented by the following formula (Ic):

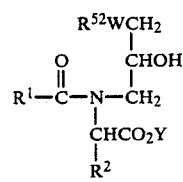

wherein $R^1$, $R^2$ and Y have the same meaning as defined above, $R^{52}$ denotes an aliphatic hydrocarbon group having 8–26 carbon atoms, and W is O or $CH_2$.

5. The external skin care preparation as claimed in claim 1, wherein the compound (I) is represented by the following formula (Id):

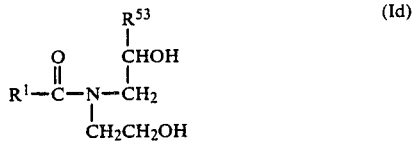

wherein $R^1$ has the same meaning as defined above, and $R^{53}$ denotes an aliphatic hydrocarbon group having 8–24 carbon atoms.

6. The external skin care preparation as claimed in claim 1, wherein the compound (I) is represented by the following formula (Ie):

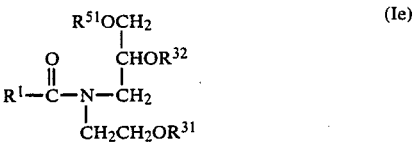

wherein $R^1$ have the same meaning as defined above, $R^{51}$ means an aliphatic hydrocarbon group having 10–26 carbon atoms, and $R^{31}$ and $R^{32}$ denote individually H, sugar residuum or group

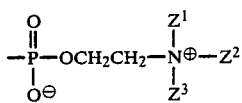

($Z^1, Z^2, Z^3$: as defined above), with a proviso that $R^{31}$ and $R^{32}$ are not H at the same time and one of $R^{31}$ and $R^{32}$ is other than the sugar residuum where the other is the group

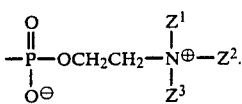

7. The external skin care preparation as claimed in any one of claims 1–6, wherein said at least one member is a surfactant.

8. A compound represented by the Formula I or a salt thereof:

wherein $R^1$ means an aliphatic hydrocarbon group having 9–25 carbon atoms, A denotes a group $+CH_2)_lOH$ (l: integer of 3–6), a group

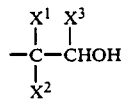

($X^1, X^2 X^3$: H, $C_{1-5}$-alkyl or hydroxyalkyl, individually), a group $(CH_2CH_2O)_m H$ (M: integer of at least 2), a group

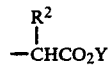

(Y: H or alkali metal; $R^2$: H, $-CH_3$,

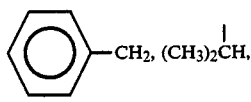

$(CH_3)_2CHCH_2-$, $C_2H_5(CH_3)CHCH_2-$, $HOCH_2-$, $CH_3(HO)CH-$, $CH_3SCH_2CH_2-$, $YOCOCH_2-$, $YOCOCH_2CH_2-$,

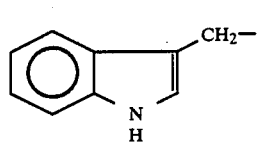

or a group $-CH_2CH_2OR^3$ [$R^3$: sugar residuum or group

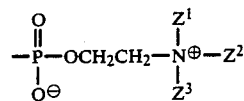

($Z^1, Z^2, Z^3$: H, straight-chain or branched $C_{1-6}$-alkyl, or aralkyl)], and B stands for a group

[$R^4$: H, sugar residuum, group

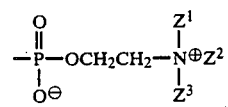

($Z^1, Z^2, Z^3$: the defined above) or group $(CH_2CH_2O)_n H$ (n: integer of at least 1); $R^5$: $C_{8-28}$-aliphatic hydrocarbon group ] or a group

($R^5$: as defined above), with a proviso that $X^1$, $X^2$, $X^3$ and $R^4$ do not mean H at the same time.

* * * * *